US009222060B2

(12) United States Patent
Barbé et al.

(10) Patent No.: US 9,222,060 B2
(45) Date of Patent: Dec. 29, 2015

(54) TRIGGERED RELEASE

(75) Inventors: Christophe Jean Alexandre Barbé, New South Wales (AU); Kim Suzanne Finnie, New South Wales (AU)

(73) Assignee: Australian Nuclear Science and Technology Organisation, New South Wales (AU)

( * ) Notice: Subject to any disclaimer, the term of this patent is extended or adjusted under 35 U.S.C. 154(b) by 360 days.

(21) Appl. No.: 13/260,653

(22) PCT Filed: Dec. 22, 2009

(86) PCT No.: PCT/AU2009/001688
§ 371 (c)(1),
(2), (4) Date: Feb. 1, 2012

(87) PCT Pub. No.: WO2010/108211
PCT Pub. Date: Sep. 30, 2010

(65) Prior Publication Data

US 2012/0021964 A1 Jan. 26, 2012

Related U.S. Application Data

(60) Provisional application No. 61/164,011, filed on Mar. 27, 2009.

(51) Int. Cl.
*A61K 9/22* (2006.01)
*A61K 38/00* (2006.01)
(Continued)

(52) U.S. Cl.
CPC *C11D 3/124* (2013.01); *C11D 3/38* (2013.01); *C11D 3/386* (2013.01); *C11D 3/38672* (2013.01); *C11D 17/0039* (2013.01); *C11D 17/06* (2013.01)

(58) Field of Classification Search
CPC . A61K 2300/00; A61K 31/22; A61K 31/365; A61K 31/40; A61K 31/405; A61K 9/22; A61K 38/00; B01J 2/08
USPC .............. 8/523; 424/464, 469, 470, 489, 491; 514/2.2; 510/320, 321, 393
See application file for complete search history.

(56) References Cited

U.S. PATENT DOCUMENTS 4,105,426 A 8/1978 Iler et al.
4,440,542 A * 4/1984 Foley ................................ 8/523
(Continued)

FOREIGN PATENT DOCUMENTS

JP 61-227520 10/1986
JP 08-012319 1/1996
(Continued)

OTHER PUBLICATIONS

International Patent Application No. PCT/AU2009/001688: International Search Report dated Mar. 5, 2010, 4 pages.
(Continued)

*Primary Examiner* — Gregory R Delcotto
*Assistant Examiner* — Preeti Kumar
(74) *Attorney, Agent, or Firm* — Baker & Hostetler LLP

(57) ABSTRACT

A method is described for delivering a species to a liquid, whereby porous particles are exposed to a condition such that the species is rapidly released into the liquid. Each of the porous particles comprises an agglomeration of primary particles so that outer surfaces of said primary particles define pores of said porous particles. The primary particles comprise silica and the species is disposed in the pores of the porous particles.

14 Claims, 12 Drawing Sheets

Emulsion droplet (water-in-oil)

Resulting Porous microparticles

(51) Int. Cl.

| | |
|---|---|
| ***B01J 2/08*** | (2006.01) |
| ***C11D 3/12*** | (2006.01) |
| ***C11D 3/38*** | (2006.01) |
| ***C11D 3/386*** | (2006.01) |
| ***C11D 17/00*** | (2006.01) |
| ***C11D 17/06*** | (2006.01) |

(56) References Cited

U.S. PATENT DOCUMENTS

| | | | | |
|---|---|---|---|---|
| 4,584,281 | A * | 4/1986 | Foley | 501/85 |
| 5,011,690 | A | 4/1991 | Garvey et al. | |
| 2003/0180549 | A1 | 9/2003 | Noguchi et al. | |
| 2009/0252808 | A1 * | 10/2009 | Finnie et al. | 424/491 |

FOREIGN PATENT DOCUMENTS

| | | |
|---|---|---|
| KR | 2005-0098072 | 10/2005 |
| WO | WO 2005/110592 | 11/2005 |
| WO | WO 2006/066317 | 6/2006 |
| WO | WO 2010/108211 | 9/2010 |

OTHER PUBLICATIONS

Wang et al., "Enzyme encapsulation in nanoporous silica spheres", Chemical Communications, Jul. 2004, Issue 13, 1528-1529.

* cited by examiner

| Time (h) | Release of Ovalbumin (% released) | |
|---|---|---|
| | Particle with 2.7 nm average pore size | Particle with 5.5 nm average pore size |
| 0 | 0 | 0 |
| 1 | 3.1 | 1.5 |
| 3 | 5.3 | 4.5 |
| 5 | 5.9 | 7.7 |
| 8 | 6.9 | 9.2 |
| 24 | 10.0 | 16.1 |

TRIGGERED RELEASE

CROSS-REFERENCE TO RELATED APPLICATIONS

This application is the National Stage of International Application No. PCT/AU2009/001688, filed Dec. 22, 2009, which claims the benefit of U.S. Provisional Application No. 61/164,011, filed Mar. 27, 2009, the disclosures of which are incorporated herein by reference in their entirety.

TECHNICAL FIELD

The present invention relates to a method for releasing an encapsulated species from particles.

BACKGROUND OF THE INVENTION

There exists currently a range of technologies for controlled release of substances from particles. These are used in a wide range of applications, from human therapeutics to industrial applications. The majority of these technologies have been directed to achieving slow, relatively constant release of an encapsulated substance. This is commonly of use therapeutically to provide a continuous effective dose of a drug and avoid large variations in concentration of the drug in bodily fluids. However certain applications require instead that an encapsulated species be released in a sudden burst on exposure to a triggering stimulus. Such applications additionally require that the encapsulated species be retained in the particles, prior to the triggering stimulus. Commonly such "triggered" release is required when encapsulation of the species in the particles provides some protection from a harsh environment.

One example of such an application is laundry detergents. Enzymes are highly desirable components of laundry detergents because of their ability to break down a range of commonly occurring stains on clothing and other fabric items (e.g. towels, table cloths, bed sheets etc). Suitable enzymes include proteases, lipases, cellulases and amylases. Liquid detergents present a challenging environment to enzymes due to their relatively high pH (about 8-9), presence of other enzymes (e.g. proteases), and detergent components such as surfactants, preservatives, and bleaches. A range of additives are commonly added in order to stabilise enzymes in the detergent formulations. Nevertheless, some enzymes, notably proteases, remain notoriously difficult to stabilise for the long shelf life required (up to 2 years).

A potential method for stabilising enzymes in liquid laundry detergents is to encapsulate them in a protective matrix which enables rapid release when added to a wash. WO2006/066317 (the contents of which are incorporated herein by cross reference) describes encapsulation of biological materials such as enzymes in silica particles for controlled release. Silica particles present an interesting option for encapsulation of laundry enzymes, as they are not dissimilar to materials already added as softening agents to laundry detergents (e.g. zeolites, silicates and citrates) in relatively high proportions (up to about 10%). Silica particles are also expected to be stable at pH about 9.0. (On increasing the pH from 9 to 10.7, there is an increase in the solubility of amorphous silica due to the formation of silicate ions in addition to monosilicic acid. Above pH=10.7, silica dissolves to form soluble silicate.)

There is a need to achieve an effective 'triggered release' of enzyme from the particles on addition of the detergent to the wash. If such a method could be achieved, the technology may also be extendable to other applications in which rapid release of a species encapsulated in particles is desired in activation by a suitable "trigger".

OBJECT OF THE INVENTION

It is the object of the present invention to at least partially, satisfy the above need.

SUMMARY OF THE INVENTION

The present invention provides a method for delivering a species to a liquid, said method comprising:

providing porous particles, said porous particles each comprising an agglomeration of primary particles whereby outer surfaces of said primary particles define pores of said porous particles, said primary particles comprising silica and said species being disposed in said pores; and exposing said porous particles to a condition whereby the species is rapidly released into the liquid.

The following options may be used in conjunction with the above method, either individually or in any suitable combination.

The porous particles may be dispersed in a diluent. The diluent may be the liquid to which the species is to be delivered. It may be some other diluent. It may be miscible with the liquid to which the species is to be delivered. The exposing may be in the presence of the liquid. In many embodiments either the porous particles are provided in the liquid or the step of exposing comprises exposing the porous particles to the liquid (e.g. dispersing the particles in the liquid).

The step of exposing the porous particles to the condition may cause the porous particles to at least partially disintegrate or deaggregate. The at least partial disintegration or deaggregation may result in release of the species from the porous particles.

The liquid may be an aqueous liquid.

The pores may have a mean diameter of about 1 to about 50 nm. The porous particles may have a mean diameter of about 0.05 to about 500 microns. The primary particles may have a mean diameter of about 5 to about 500 nm.

The species may be a biological species. It may be, or may comprise, a protein, a peptide, an oligopeptide, a synthetic polypeptide, a saccharide, a polysaccharide, a glycoprotein, an enzyme, DNA, RNA, a DNA fragment or a mixture of any two or more of these. It may be, or may comprise, some other macromolecular species. It may be, or may comprise, a polymer, e.g. a polymeric dye. It may be, or may comprise, a particulate species. It may be, or may comprise, cells or viral particles. The species may be any suitable species that is sufficiently large (e.g. has sufficiently large diameter) to remain encapsulated by the porous particles and not be released to a substantial degree until the porous particles are exposed to the condition leading to rapid release of said species.

The condition may be such that the silica of the primary particles at least partially dissolves or hydrolyses so as to rapidly release the species. It may be such that bridges joining the primary particles at least partially dissolve or hydrolyse. Said dissolution or hydrolysis may result in at least partial disintegration or deaggregation of the porous particles. It may result in rapid release of the species. The dissolution or hydrolysis may represent an "unzipping" or deesterification of Si—O—Si linkages which form said bridges. The condition may comprise sufficient dilution in the liquid for release of the species from the porous particles. The sufficient dilution may result in a dissolved silica concentration significantly less than the solubility limit of silica in the liquid (about 0.12 mg/mL in water at neutral pH at ambient temperature) or a ratio of silica particles to liquid of less than about 250 ppm on a w/v basis. The condition may be dilution, temperature, pH or a combination of any two or all of these.

The species may be protected from degradation or denaturation by encapsulation in said porous particles prior to release therefrom.

The step of providing the dispersion may comprise:

preparing a mixture of colloidal silica and the species;

combining the mixture with a solution of a surfactant in a solvent so as to form an emulsion, said emulsion comprising the mixture as a dispersed phase and the solvent as a continuous phase; and allowing the colloidal silica in the dispersed phase to form the porous particles having the species in pores thereof.

The method may comprise reducing the pH of the colloidal silica. This may be conducted before preparing the mixture. It may be conducted concurrently with preparing the mixture. It may be conducted after preparing the mixture, in which case it may represent reducing the pH of the mixture. It may be conducted after forming the emulsion. It may be conducted before forming the emulsion.

The method may additionally comprise separating the porous particles from the solvent and washing the porous particles. It may additionally comprise dispersing the porous particles in the liquid.

The method may be such that it does not comprise drying the porous particles.

The mixture described in the step of providing the dispersion may additionally comprise a protectant for protecting the species from degradation or denaturation. The protectant may comprise calcium ions and/or potassium ions and/or glycerol and/or sugars such as glucose, lactose etc. and/or some other suitable protectant. It may comprise a mixture of any two or more of these.

The release of the species from the porous particles may occur within about 15 minutes of exposing the porous particles to the condition.

In an embodiment there is provided a method for delivering a species to an aqueous liquid, said method comprising:

providing a dispersion of porous particles in the liquid, said porous particles each comprising an agglomeration of primary particles whereby outer surfaces of said primary particles define pores of said porous particles, said primary particles comprising silica and said species being disposed in said pores; and exposing said porous particles to a condition whereby the porous particles at least partially disintegrate so as to rapidly deliver the species to the liquid.

In another embodiment there is provided a method for delivering a species, e.g. an enzyme, to an aqueous liquid, said method comprising:

providing a dispersion of porous particles in a liquid detergent formulation, said porous particles each comprising an agglomeration of primary particles whereby outer surfaces of said primary particles define pores of said porous particles, said primary particles comprising silica and said species being disposed in said pores; and diluting the dispersion in an aqueous liquid such that the silica concentration is significantly less than the solubility limit of silica in the liquid or such that the ratio of silica particles to aqueous liquid is less than about 250 ppm on a w/v basis, whereby the porous particles at least partially disintegrate so as to rapidly deliver the species to the aqueous liquid.

In another embodiment there is provided a method for delivering a species to an aqueous liquid, said method comprising:

preparing a mixture of colloidal silica and the species;

adjusting said mixture to an alkaline pH;

combining the alkaline mixture with a solution of a surfactant in a solvent so as to form an emulsion, said emulsion comprising the alkaline mixture as a dispersed phase and the solvent as a continuous phase;

allowing the colloidal silica in the dispersed phase to form the porous particles having the species in pores thereof; and exposing said porous particles to a condition whereby the porous particles at least partially disintegrate so as to rapidly deliver the species to the liquid.

In another embodiment there is provided a method for delivering a species, e.g. an enzyme, to an aqueous liquid, said method comprising:

preparing a mixture of colloidal silica and the species;

adjusting said mixture to an alkaline pH;

combining the alkaline mixture with a solution of a surfactant in a solvent so as to form an emulsion, said emulsion comprising the alkaline mixture as a dispersed phase and the solvent as a continuous phase;

allowing the colloidal silica in the dispersed phase to form the porous particles having the species in pores thereof;

forming a suspension of the particles in a liquid detergent formulation;

storing said suspension, whereby the species is protected from degradation; and diluting the suspension in an aqueous liquid such that the silica concentration is significantly less than the solubility limit of silica in the liquid or such that the ratio of silica particles to aqueous liquid is less than about 250 ppm on a w/v basis, whereby the porous particles at least partially disintegrate so as to rapidly deliver the species to the aqueous liquid.

In another embodiment there is provided a method for delivering a species to an aqueous liquid, said method comprising:

adjusting a sample of colloidal silica to a desired pH;

dissolving the species in the pH adjusted colloidal silica to form a silica/species mixture;

combining the silica/species mixture with a solution of a surfactant in a solvent so as to form an emulsion, said emulsion comprising, the silica/species mixture as a dispersed phase and the solvent as a continuous phase;

allowing the colloidal silica in the dispersed phase to form the porous particles having the species in pores thereof; and exposing said porous particles to a condition whereby the porous particles at least partially disintegrate so as to rapidly deliver the species to the liquid.

The desired pH may be an alkaline pH. It may be for example between about 7.5 and 9.5, e.g. about 7.5, 8, 8.5, 9 or 9.5. It may be a neutral pH. It may be about pH 7. It may be an acidic pH, e.g. between about 6.5 and about 3. It may be a pH at which the species is substantially stable.

In another embodiment there is provided a method for delivering a species, e.g. an enzyme, to an aqueous liquid, said method comprising:

adjusting a sample of colloidal silica to a desired pH;

dissolving the species in the pH adjusted colloidal silica to form a silica/species mixture;

combining the silica/species mixture with a solution of a surfactant in a solvent so as to form an emulsion, said emulsion comprising the silica/species mixture as a dispersed phase and the solvent as a continuous phase;

allowing the colloidal silica in the dispersed phase to form the porous particles having the species in pores thereof;

forming a suspension of the particles in a liquid detergent formulation;

storing said suspension, whereby the species is protected from degradation; and diluting the suspension in an aqueous liquid such that the silica concentration is significantly less than the solubility limit of silica in the liquid or such that the ratio of silica particles to aqueous liquid is less than about 250 ppm on a w/v basis, whereby the porous particles at least partially disintegrate so as to rapidly deliver the species to the aqueous liquid.

The desired pH may be an alkaline pH. It may be for example between about 7.5 and 9.5, e.g. about 7.5, 8, 8.5, 9 or 9.5. It may be a neutral pH. It may be about pH 7. It may be an acidic pH, e.g. between about 6.5 and about 3. It may be a pH at which the species is substantially stable.

In another embodiment there is provided a method for delivering a species (e.g. RNA, or DNA or a protein stable in acid such as pepsin) to an aqueous liquid, said method comprising:

adjusting a sample of colloidal silica to a desired pH;

dissolving the species in the pH adjusted colloidal silica to form a silica/species mixture;

combining the silica/species mixture with a solution of a surfactant in a solvent so as to form an emulsion, said emulsion comprising the silica/species mixture as a dispersed phase and the solvent as a continuous phase;

allowing the colloidal silica in the dispersed phase to form the porous particles having the species in pores thereof;

forming a suspension of the particles in a liquid detergent formulation;

storing said suspension, whereby the species is protected from degradation; and diluting the suspension in an aqueous liquid such that the silica concentration is significantly less than the solubility limit of silica in the liquid or such that the ratio of silica particles to aqueous liquid is less than about 250 ppm on a w/v basis, whereby the porous particles at least partially disintegrate so as to rapidly deliver the species to the aqueous liquid.

The desired pH may be an acidic pH. It may be for example between about 5 and about 3, e.g. about 5, 4.5, 4, 3.5, or 3.0. The lower limit for the desired pH may depend on the stability of the species.

In another embodiment the species is an enzyme for use in laundry applications. In this case the method may comprise adding a dispersion of porous particles in a detergent formulation to an aqueous liquid as a step in a process of washing laundry items. The porous particles may each comprise an agglomeration of primary particles whereby outer surfaces of said primary particles define pores of said porous particles. The primary particles comprise silica and said species is disposed in said pores. The porous particles may be made by a process comprising preparing a mixture of colloidal silica and the enzyme; combining the mixture with a solution of a surfactant in a solvent so as to form an emulsion, said emulsion comprising the mixture as a dispersed phase and the solvent as a continuous phase; and allowing the colloidal silica in the dispersed phase to form the porous particles having the enzyme in pores thereof. In this embodiment, the adding is conducted so as to dilute said porous particles in the aqueous liquid to a degree sufficient to cause at least partial disintegration of the porous particles, whereupon the porous particles rapidly release the species so as to deliver the species to the aqueous liquid in order to assist in said process of washing.

In another aspect, the invention provides a method for delivering a species to a liquid, said method comprising:

preparing a mixture of colloidal silica and the species;

combining the mixture with a solution of a surfactant in a solvent so as to form an emulsion, said emulsion comprising the mixture as a dispersed phase and the solvent as a continuous phase;

allowing the colloidal silica in the dispersed phase to form porous particles having the species in pores thereof;

optionally storing said porous particles; and exposing said porous particles to a condition whereby the species is rapidly released into the liquid.

In a further aspect, the invention provides a method for delivering a species to a liquid, said method comprising:

providing porous particles which are made by a process comprising preparing a mixture of colloidal silica and the species; combining the mixture with a solution of a surfactant in a solvent so as to form an emulsion, said emulsion comprising the mixture as a dispersed phase and the solvent as a continuous phase; and allowing the colloidal silica in the dispersed phase to form the porous particles having the species in pores thereof; and exposing said porous particles to a condition whereby the species is rapidly released into the liquid.

Many of the options described in conjunction with the first mentioned aspect above may be used in conjunction with the second and third mentioned aspects, in particular (but not limited to) the nature of the particles and of the particles of colloidal silica, features of making the porous particles, details of the condition for rapid release of the species and the nature of the species.

In a further aspect of the invention there is provided the use of porous particles for rapidly delivering a species to a liquid. The particles may be made by a process comprising preparing a mixture of colloidal silica and the species; combining the mixture with a solution of a surfactant in a solvent so as to form an emulsion, said emulsion comprising the mixture as a dispersed phase and the solvent as a continuous phase; and allowing the colloidal silica in the dispersed phase to form the porous particles having the species in pores thereof. The particles may each comprising an agglomeration of primary particles whereby outer surfaces of said primary particles define pores of said porous particles, said primary particles comprising silica and said species being disposed in said pores.

The use may be such that the particles are undried.

Disclosed herein are also porous particles for use in rapidly delivering a species to a liquid, said particles being made by a process comprising:

preparing a mixture of colloidal silica and the species;

combining the mixture with a solution of a surfactant in a solvent so as to form an emulsion, said emulsion comprising the mixture as a dispersed phase and the solvent as a continuous phase; and allowing the colloidal silica in the dispersed phase to form the porous particles having the species in pores thereof.

Disclosed herein are also porous particles for use in rapidly delivering a species to a liquid, said particles each comprising an agglomeration of primary particles whereby outer surfaces of said primary particles define pores of said porous particles, said primary particles comprising silica and said species being disposed in said pores.

Disclosed herein is also a process for making porous particles for use in rapidly delivering a species to a liquid, said process comprising:

preparing a mixture of colloidal silica and the species;

combining the mixture with a solution of a surfactant in a solvent so as to form an emulsion, said emulsion comprising the mixture as a dispersed phase and the solvent as a continuous phase; and allowing the colloidal silica in the dispersed phase to form the porous particles having the species in pores thereof.

BRIEF DESCRIPTION OF THE DRAWINGS

A preferred embodiment of the present invention will now be described, by way of an example only, with reference to the accompanying drawings wherein.

DETAILED DESCRIPTION OF THE PREFERRED EMBODIMENTS

Figure 1:
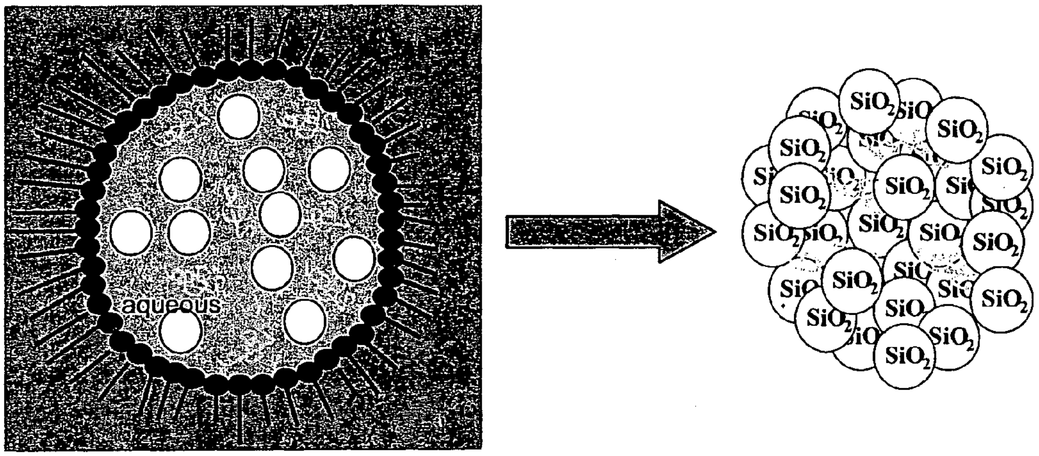
FIG. 1 is a diagram of aggregation of primary colloidal silica particles to produce porous particles.

WO2006/066317 (the entire contents of which are incorporated herein by cross reference) described a process for releasably encapsulating a biological entity in porous particles. The process comprises the steps of forming an emulsion comprising emulsion droplets dispersed in a non-polar solvent, wherein the emulsion droplets comprise colloidal silica and a biological entity (e.g. a protein, enzyme etc.), and forming particles from the emulsion droplets, said particles having the biological entity therein and/or thereon. In the step of forming the emulsion, a first emulsion may be formed from the non-polar solvent, a surfactant and the colloidal silica, and the biological entity combined with the first emulsion, or a first emulsion may be formed from the non-polar solvent, a surfactant and the biological entity, and the colloidal silica combined with that emulsion, or the biological entity may be combined with the colloidal silica and the resulting mixture combined with the non-polar solvent and surfactant to form the emulsion, or some other order of addition could be employed. Release of the biological entity from the particles was shown to depend in part on the size of the particles of the colloidal silica used to make them. It was hypothesised that the colloidal silica particles aggregated to form the porous particles as agglomerates, in which spaces between the aggregated colloidal silica particles represented pores of the porous particles. Release also depended on the size of the encapsulated biological entity. Release was shown to occur over an extended period of time, commonly hours, days or even weeks. FIG. 1 shows a diagram of aggregation of primary colloidal silica particles to produce porous particles having an entity trapped in the pores thereof.

In pure water (neutral pH), amorphous silica dissolves to give a solution approximately 120 ppm in soluble silica, largely present as monosilicic acid ($Si(OH)_4$). This presents a limit to the extent of dissolution of particles added to aqueous solution. However, dilution with a relatively large amount of water can provide a mechanism for causing more extensive dissolution. In the case of particles synthesised using colloidal silica, complete dissolution is not considered necessary to release a large proportion of encapsulated actives. What is thought to be required is rather a rapid deaggregation of the particles to smaller fragments of the, original colloidal material used to construct the particles.

Figure 2:
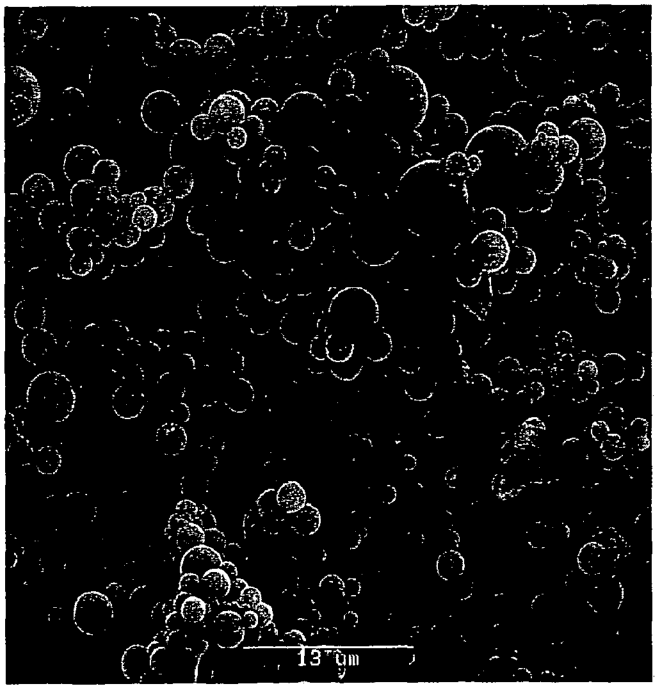
FIG. 2 is a micrograph of porous microparticles used in the present invention.
Figures 3, 4:
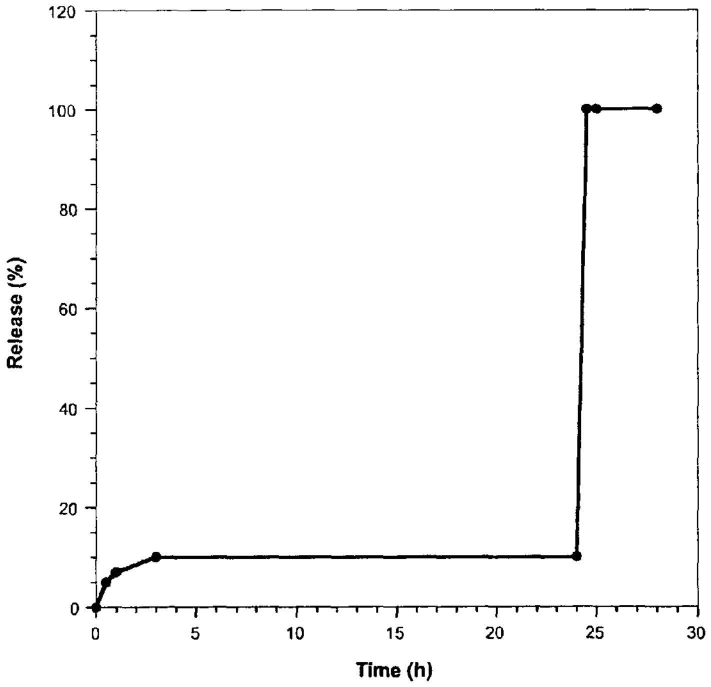
FIG. 3 shows typical slow release data from porous particles.
FIG. 4 is a simulated curve of release of encapsulated species over time.

A micrograph of the porous particles is shown in FIG. 2. Encapsulation of a wide range of peptides, enzymes, proteins and DNA etc. is possible using the method of WO2006/066317, and a variety of particle sizes is achievable. The particles may readily be produced while preserving the integrity of the encapsulated species by using bio-friendly chemistry. Release was found to take place by diffusion through the porous network of the porous particles. The release rate in that case depends on the pore size and the size of the encapsulated entity. Release start upon immersion in a suitable liquid. Typical release data are shown in FIG. 3 for release of ovalbumin over a 24 hour period. It can be seen that under the conditions used in WO2006/066317, release is relatively slow.

For certain applications, such slow release is undesirable. One such application is in laundry detergents in which enzymes are encapsulated in the porous particles. For this application it is desirable that little or no release of enzyme occurs in concentrated laundry detergent and that rapid release of enzyme occurs on dilution in water. Further, preservation of enzyme activity is required during storage. FIG. 4 shows a simulated release curve with an approximation to the desired release profile, which simulates the case where the dilution occurs at about 24 hours, leading to rapid and substantially total release of the entire encapsulated species.

The inventors have now surprisingly found that these particles may be used to release their payload (i.e. the encapsulated species) rapidly on exposure to a suitable condition or trigger, and to restrict release in the absence of the release.

In certain embodiments, the trigger is essentially a rapid dilution into water. Upon dilution, the silica concentration goes below the solubility limit, and it is thought that the small link between the colloidal particles "unzips" i.e. hydrolyzes. This results in the encapsulated species being liberated by disintegration and/or de-agglomeration of the matrix of the porous particles.

Investigations using a variety of silica precursors and pretreatment conditions prior to encapsulation have indicated that modification of the internal pore structure of the host particle plays an important role in determining the rate of active release both in concentrated and diluted conditions. The ideal pore size appears to be one which restricts the diffusion of the encapsulated species in concentrated conditions, but is sufficiently large to allow rapid diffusion of water leading to disintegration of the porous particles on dilution (see examples below). Another important factor is the particle size of the porous particles. In general, the smaller the particle size, the faster the disintegration on dilution.

It is hypothesised that suitable triggers are conditions which cause at least partial deaggregation of the porous particles, thereby leading to rapid release of the encapsulated species. As described in WO2006/066317, the release of an encapsulated species depends to some degree at least on the relative sizes of the pores of the porous particle and the species. Thus if the species is larger than the pores, release will be retarded or prevented. The sizes of the pores may be tailored by suitable choice of colloidal silica used in making the porous particles. Thus a smaller particle size colloidal silica will result in a smaller size of pores in the resulting porous particle. Thus in the present invention, the pore size of the porous particles may be tailored so as to be smaller than the encapsulated entity, so as to restrict or prevent release of the entity by a diffusion mechanism. The pore size may also depend on the pH to which the colloidal silica is adjusted prior to formation of an emulsion. For example when particles were made from colloidal silica Bindzil® 30/360 which had been reduced to pH 7.5, the resulting particles had an average pore size of 8.7 nm, whereas if the same colloidal silica was used at pH 10, the resulting particles had a pore size of 5.9 nm. Reducing the pH once the colloidal silica has already been added to the emulsion appeared to have no effect on the pore size.

Accordingly, the present invention provides a method for delivering a species to a liquid. The method comprises exposing porous particles to a condition whereby the species is rapidly released into the liquid. The porous particles may each comprise an agglomeration of primary silica particles (derived from particles of colloidal silica) whereby outer surfaces of said primary particles define pores of said porous particles and the species is disposed in the pores of the porous particles. They may be made by a process comprising preparing a mixture of colloidal silica and the species; combining the mixture with a solution of a surfactant in a solvent so as to form an emulsion, said emulsion comprising the mixture as a dispersed phase and the solvent as a continuous phase; and allowing the colloidal silica in the dispersed phase to form the porous particles having the species in pores thereof. The porous particles prior to the release of the species may be dispersed in a diluent. The diluent may be an aqueous diluent. It may be the liquid into which the species is to be released, or the liquid into which the species is to be released may comprise the diluent. In one example, the porous particles are provided as a dispersion in a detergent as diluent, and the condition for rapid release of an encapsulated species is sufficient dilution in an aqueous liquid to cause said rapid release. The step of exposing the porous particles to the condition may comprise combining the particles and the liquid. It may comprise exposing the porous particles in the liquid to the condition.

In some embodiments of the invention the pores of the particles are sufficiently small relative to the size of the encapsulated species that the encapsulated species can not diffuse through the pores of the particles to as to release from the particles. In these embodiments, the only available release mechanisms for the encapsulated species are very slow release by dissolution of the matrix of the particles and rapid release by deaggregation as described herein. Since the conditions for rapid release (as described herein) are similar to those that would encourage dissolution of the matrix, in these embodiments the particles would either not release the encapsulated species or would release it rapidly (depending on the selected conditions). In other embodiments the pores of the particles are sufficiently large to allow diffusion of the encapsulated species through the pores. In this case, depending on the conditions used (which may be selected at will), the release of the encapsulated species may be rapid (by deaggregation as described herein) or slow (by diffusion under conditions where the particles remain essentially intact).

The particles used in the present invention comprise primary particles which comprise silica. The primary particles may consist essentially of silica. They may consist of silica. The primary particles may be silicon dioxide. They may be surface modified with covalently bound organic substituents, such as alkyl groups (methyl, ethyl, propyl etc.) or other groups such as thiols, amines, hydroxyl groups, vinyl groups, or epoxy groups, or more than one of these.

The method of the present invention may be such that it does not comprise treatment of a human. It may be such that it does not comprise diagnosis of a condition in a human. It may be such that it does not comprise treatment of a human or of a non-human animal. It may be such that it does not comprise diagnosis of a condition in a human or of a non-human animal. It may be a non-therapeutic method. It may be a non-diagnostic method.

It is thought that the rapid release is caused by at least partial disintegration and/or deagglomeration of the porous particles. In the absence of such disintegration or deagglomeration the inventors consider that the only mechanisms for release would be either slow dissolution of the matrix of the porous particles or diffusion of the species out of the pores of the porous particles. Neither,of these mechanisms would provide the rapid release of the present invention. Further, in the event that the pore size is smaller than the diameter of the encapsulated species, the diffusion mechanism will be precluded.

Commonly the liquid into which the species is delivered is an aqueous liquid. It may be water, or it may be an aqueous solution, suspension and/or emulsion. Prior to the triggered release of the present method, the particles may not be present in a liquid or they may be present in either the aqueous liquid or in some other liquid. In the case where the particles are not in a liquid, it is preferable that they are not dried, as drying of the particles may retard the release on exposure to the trigger condition.

In a particular example, the species is useful in laundry applications (e.g. an enzyme) and the particles prior to the release are present in a liquid detergent formulation. Once the liquid detergent formulation is added to a wash and exposed to an aqueous environment, the trigger condition may trigger rapid release of the species. The liquid detergent formulation may be saturated in silica, so that, in the absence of further dilution, the particles can not deagglomerate (so as to release the species) by partial dissolution of the silica particles.

The trigger condition may be any suitable condition capable of causing rapid release of the species to the liquid. Suitable trigger conditions include those which cause the porous particles to at least partially disintegrate or deaggregate. These may be conditions which promote partial dissolution of the silica of the particles in the liquid. Thus for example under high dilution conditions, sufficient dissolution of the silica is thought to occur to effect at least partial disintegration of the porous particles. It will be recognised that only sufficient dissolution is required to weaken the fusion regions between the primary particles in order to effect disintegration, and that not all of the fusion points need to be dissolved in order to result in rapid release of the species. Thus the trigger condition may be a dilution in an aqueous liquid sufficient to result in the rapid release of the species. The dilution may be such that the ratio of silica particles to liquid (e.g. aqueous liquid) is less than about 250 ppm on a w/v basis, or less than about 200, 150, 100 or 50 ppm, or about 1 to about 250 ppm on a w/v basis, or about 10 to 250, 50 to 250, 100 to 250, 1 to 150, 1 to 100, 1 to 50, 1 to 10, 10 to 150, 50 to 150, 100 to 150, 50 to 100 or 10 to 50 ppm, e.g. about 1, 2, 3, 4, 5, 6, 7, 8, 9, 10, 20, 30, 40, 50, 60, 70, 80, 90, 100, 150, 200 or 250 ppm on a w/v basis. In some cases it may be even more dilute than 1 ppm. The dilution may be dependent on the pH of the liquid. Thus a more alkaline liquid may require not require as high a dilution as would a less alkaline liquid.

Other trigger conditions may include a sufficiently high temperature to rapidly release the particles. Solubility of silica in aqueous liquids will increase with increasing temperature. Thus if the concentration of the particles in the liquid is such that rapid release does not occur at a first temperature, raising the temperature to a second (higher) temperature may lead to sufficient dissolution of the silica as to cause rapid release of the species. The difference between the first and second temperatures may be for example at least about 10 Celsius degrees, or at least about 20, 30, 40 or 50 Celsius degrees, or may be about 10 to about 50 Celsius degrees, or about 10 to 30, 20 to 50 or 20 to 40 Celsius degrees, e.g. about 10, 20, 30, 40 or 50 Celsius degrees. The second temperature may for example be at least about.50, 60, 70, 80 or 90° C., or about 50 to about 90° C., or about 50 to 70, 70 to 90 or 60 to 80° C., e.g. about 50, 60, 70, 80 or 90° C. A further trigger condition may be pH. It is known that silica dissolves rapidly at high pH. Thus the trigger condition may be a pH of greater than about 9, or greater than about 9.5, 10, 10.5 or 11, or about 9 to 12, 10 to 12, 9 to 11, 9 to 10 or 10 to 11, e.g. about 9, 9.5, 10, 10.5, 11, 11.5 or 12. It will be understood that the trigger condition may be any suitable combination of temperature, pH and concentration which leads to rapid release of the encapsulated species. The precise nature of the trigger condition may be determined with reference to the conditions which promote stability of the encapsulated entity. Thus for example many proteins will not be stable to conditions of high pH, or to high temperatures, and would denature under such conditions. High dilution may be a suitable trigger condition for use with such entities.

From the foregoing it is clear that the rapid release of the species from the porous particles may represent, or may be precipitated by, at least partial decomposition, or at least partial deaggregation, or at least partial deagglomeration, of the porous particles. The at least partial decomposition or deaggregation or deagglomeration may generate separated primary particles, said primary particles being those of which the porous particles were comprised prior to said at least partial decomposition or deaggregation or deagglomeration.

The rapid release of the species from the porous particles may occur within about 30 minutes, or within about 15 minutes, of exposing the porous particles to the condition. It may occur within about 14, 13, 12, 11, 10, 9, 8, 7, 6, 5, 4, 3, 2 or 1 minute of exposing the porous particles to the condition. At least about 50% of the species may be released from the porous particles within about 15 minutes of exposing the porous particles to the condition, or at least about 60, 70, 80, 90, 95 or 99% of the species may be released within about 15 minutes. At least about 50% of the species may be released from the porous particles within about 10 minutes of exposing the porous particles to the condition, or at least about 60, 70, 80, 90, 95 or 99% of the species may be released within about 10 minutes. At least about 50% of the species may be released from the porous particles within about 5 minutes of exposing the porous particles to the condition, or at least about 60, 70, 80, 90, 95 or 99% of the species may be released within about 5 minutes. At least about 50% of the species may be released from the porous particles within about 2 minutes of exposing the porous particles to the condition, or at least about 60, 70, 80, 90, 95 or 99% of the species may be released within about 2 minutes. At least about 50% of the species may be released from the porous particles within about 1 minute of exposing the porous particles to the condition, or at least about 60, 70, 80, 90, 95 or 99% of the species may be released within about 1 minute. Rapid release of the species from the porous particles may occur within about 1 to about 30 minutes, or within about 1 to about 15 minutes, of exposing the porous particles to the condition, or within about 1 to 10, 1 to 5, 1 to 2, 2 to 15, 5 to 15, 10 to 15, 5 to 10 or 2 to 5, or it may occur in less time than this, e.g. about 10 seconds to about 1 minute, or about 10 to 30 seconds or 30 seconds to 1 minute. Within this time, the proportion of the species released may be about 50 to about 100%, or about 50 to 90, 50 to 70, 70 to 100, 90 to 100, 70 to 90, 90 to 99, 90 to 95 or 95 to 99%. The rate of release may depend on the nature of the condition which initiates the release. It may be dependent on the pH of the liquid into which the species is released. It may depend on the temperature at which the release is conducted. It may depend on the concentration of the particles in the liquid into which the species is released.

The pores of the porous particles may have a mean diameter of about 1 to about 50 nm, or about 1 to 20, 1 to 10, 1 to 5, 5 to 50, 10 to 50, 20 to 50, 5 to 20, 15 to 10 or 10 to 20 nm, e.g. about 1, 2, 3, 4, 5, 10, 15, 20, 25, 30, 35, 40, 45 or 50 nm. The pore size may depend on the nature of the colloidal silica used to make the porous particles. In general, a larger particle size of colloidal silica will produce a larger pore size of the resulting particles. It is thought that this results from the pores being formed as the spaces between the aggregated colloidal particles of silica (primary particles). The primary particles may have a mean diameter of about 2 to about 500nm, or about 2 to 100, 2 to 50, 2 to 20, 2 to 10, 5 to 500 nm, 5 to 100, 5 to 50, 5 to 20, 5 to 10, 10 to 500, 100 to 500, 10 to 100, 10 to 50 or 50 to 100 nm, e.g. about 2, 3, 4, 5, 10, 15; 20, 25, 30, 35, 40, 45, 50, 60, 70, 80, 90, 100, 150, 200, 250, 300, 350, 400, 450 or 500 nm. The porous particles may have a mean diameter of about 0.05 to about 500 microns, or about 0.05 to 100, 0.05 to 20, 0.05 to 10, 0.05 to 1, 0.05 to 0.5, 0.1 to 500, 1 to 500, 10 to 500, 100 to 500, 1 to 100, 1 to 20, 1 to 10, 10 to 100, 50 to 100 or 100 to 300 microns, e.g. 0.05, 0.1, 0.5, 1, 2, 3, 4, 5, 6, 7, 8, 9, 10, 20, 30, 40, 50, 60, 70, 80, 90, 100, 150, 200, 250, 300, 350, 400, 450 or 500 microns. They may have a broad particle size distribution.

The species may be a biological species. It may be a protein, a peptide, an oligopeptide, a saccharide, a synthetic polypeptide, a polysaccharide, a glycoprotein, an enzyme, DNA, RNA, a DNA fragment, an $F_{ab}$, an $F_c$, an antibody or a mixture of any two or more of these. It may be a base resistant species, e.g. a base resistant protein such as alkyl phosphatase. It may be an acid resistant species, e.g. an acid resistant (commonly Mild acid resistant) protein such as pepsin, albumin etc. It may for example be an enzyme for use in laundry applications. It may be a protease. It may be for example subtilisin. It may be some other type of species. In some instances it may be a virus or a monocellular organism (e.g. bacteria) or may be some other particulate (e.g. nanoparticulate) species. In other instances it may be a macromolecular species, e.g. a polymer. It may be a synthetic polymer. It may be a natural polymer. It may be a therapeutic agent, for example a macromolecular or polymeric therapeutic agent. The species may be such that it does not substantially adhere to the surfaces of the primary particles. This may facilitate release of the species into the liquid during and/or following deaggregation of the porous particles. The primary particles may be such that the species does not substantially adhere to the surfaces thereof.

The species may be present in the porous particles at up to about 15% by weight, or up to about 10% by weight, or up to about 5, 2, or 1% by weight. It may be present at about 0.1 to 15%, or about 0.1 to about 10%, or about 0.5 to 10, 1 to 10, 2 to 10, 5 to 10, 10 to 15, 10 to 13, 0.1 to 1, 0.1 to 0.5, 0.5 to 5, 0.5 to 2 or 1 to 5%, e.g. about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14 or 15% by weight. In some instances it may be present in greater than 10% by weight or greater than about 15% by weight. The porous particles may comprise at least about 60% silica, or at least about 65, 70, 75, 80, 85 or 90% silica, or about 60 to about 95% silica, or about 60 to 90, 60 to 80, 70 to 95, 90 to 95, 70 to 90 or 70 to 80%, e.g. about 60, 65, 70, 75., 80, 85, 90 or 95% silica by weight. The material accounting for the remainder of the weight of the particles may comprise the releasable species, water etc.

The species may be protected from degradation or denaturation by encapsulation in said porous particles prior to release therefrom. Commonly the encapsulation of the species in the pores of the porous particles provides an environment favourable to the species. Thus encapsulation of the species in the porous particles may facilitate storage of the species without substantial degradation. The species may be stored in an otherwise hostile environment, e.g. in a region of unfavourable pH, in a detergent formulation etc., without substantial degradation. The rate of degradation of the species encapsulated in the porous particles may be less than 50% of the rate in the same medium but not encapsulated, or less than 20, 10, 5, 2 or 1%. This ratio will depend in part on the nature of the medium. In a medium that is hostile to the species, the reduction in rate of degradation will be greater than in a less hostile medium.

Figure 5:
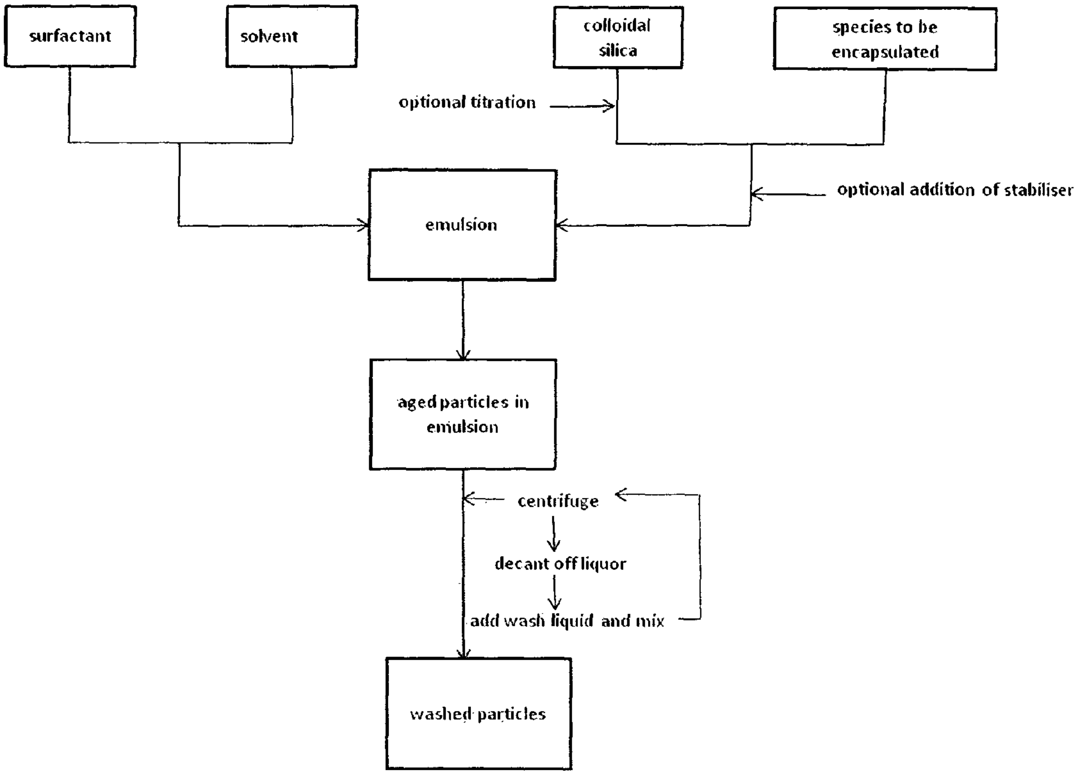
FIG. 5 is a scheme for formation of the porous particles used in the present method.

FIG. 5 shows a scheme illustrating an example of the formation of the porous particles used in the present method.

Examples of processes for producing the porous particles used in the present invention include:

Process 1:

reduce pH of colloidal silica to about pH 9 by addition of a mineral acid;

dissolve the species to be encapsulated in the colloidal silica at about pH 9;

add the colloidal silica/species mixture to a solution of surfactant in non-polar solvent with stirring;

after about 2 mins, add water;

reduce pH using a mineral acid;

stir for 4 hours, then centrifuge to settle the particles;

wash the particles with a non-polar solvent.

Process 2:

dissolve surfactant in non-polar solvent with stirring;

reduce colloidal silica to pH about 7.5 by addition of mineral acid;

dissolve species to be encapsulated in the pH 7.5 colloidal silica with stirring;

add the species/colloidal silica mixture to the surfactant/non-polar solvent solution with stirring;

add water at pH 9;

add an acidic $Ca^{2+}$ solution;

after stirring for about 4 hours, transfer the solution to a falcon tube, and centrifuge;

add a non-polar solvent to the tube and stir, then centrifuge again;

wash the solids three times, centrifuging remove the supernatant each time.

The particles may therefore be made by a process incorporating the following steps:

preparing a mixture of colloidal silica and the species: colloidal silica is commonly highly alkaline. Such conditions are often hostile to the types of species encapsulated in the present invention. It may be convenient to adjust the pH of the colloidal silica to a less highly alkaline pH prior to addition of the species. This may be achieved by addition of an acid, or of a buffer. Suitable acids include mineral acids such as hydrochloric acid, sulphuric acid etc. Suitable pHs will depend on the nature of the species, but are typically mildly alkaline to neutral. They may be for example about 7 to about 9.5, or about 7 to 9, 7 to 8.5, 7 to 8, 8 to 9.5 or 8 to 9, e.g. about 7, 7.5, 8, 8.5, 9 or 9.5. The pH may be acidic. It may be about 3 to about 7, or about 4, to 7, 5 to 7, 6 to 7 or 4 to 6. The pH may be such that the encapsulated species is not substantially denatured or otherwise adversely affected by the pH. The choice of the adjusted pH is preferably selected so as to achieve a suitable rate of gelation. Thus it is preferable to choose a pH that does not induce extremely rapid gelation, since this has been observed to result in an amorphous gel rather than well defined agglomerate particles. One may define a pH of maximum rate as that pH at which the maximum rate of gelation occurs. This pH may be the point of zero charge of the primary particles of the colloidal silica. It may be the isoelectric point of the colloidal silica. It may be in the range of about 5.5 to about 6. It may be affected by such factors as the presence/concentration of various ions, e.g. $Ca^{2+}$, temperature etc. It is preferable that the adjusted pH is at least about 0.2 pH units away from the pH of maximum rate (either above or below), or at least about 0.3, 0.5, 0.5, 0.6, 0.7, 0.8, 0.9 or 1 pH unit away, or about 0.2 to about 3.5 pH units away, or about 0.2 to 3, 0.2 to 2, 0.2 to 1, 0.5 to 3.5, 0.5 to 3, 0.5 to 2, 1 to 3.5, 2 to 3.5 or 1 to 3 pH units away. The particular pH may therefore depend on the exact chemistry of the system and the nature of the species to be encapsulated. In some cases, the pH may be adjusted after or concurrently with combining the colloidal silica and the species. Similar ranges of pH are suitable in this case. Typical ratios of species to colloidal silica are about 10 to about 100 mg/ml, and may be about 10 to 50, 10 to 20, 20 to 100, 50 to 100 or 20 to 50mg/ml, e.g. about 10, 20, 30, 40, 50, 60, 70, 80, 90 or 100 mg/ml.

combining the mixture with a solution of a surfactant in a solvent so as to form an emulsion, said emulsion comprising the mixture as a dispersed phase and the solvent as a continuous phase: typically the mixture will be added at about 1 to about 10% by weight of the solution, or about 1 to 5, 1 to 2, 2 to 10, 5 to 10 or 2 to 5%, e.g. about 1, 2, 3, 4, 5, 6, 7, 8, 9 or 10%. Suitable surfactants include Span 20 (sorbitan monolaurate), other Span surfactants (e.g. 40, 60, 80), Aerosol OT and nonophenol-6-ethoxylate, however other surfactants capable of stabilising a water in oil emulsion may be used. The surfactant may be used in a ratio of about 5 to about 30% by weight in the solvent, or about 5 to 20, 5 to 10, 10 to 30, 20 to 30 or 15 to 25%, e.g. about 5, 10, 15, 20, 25 or 30%: The solvent should not be water miscible. It may have sufficiently low miscibility with water that an emulsion may be formed. It may be a non-polar solvent. It may be a hydrocarbon solvent. It may be an aliphatic solvent. It may be for example kerosene, hexane, cyclohexane, pentane, octane, heptane, toluene or some other suitable solvent. It may be an oil, e.g. vegetable oil, paraffin oil, etc. The solvent and surfactant may be such as to have the minimum effect on the activity or integrity of the encapsulated species e.g. to avoid denaturation of an encapsulated enzyme. The resulting emulsion is a water in oil (W/O) emulsion. It comprises droplets of the mixture dispersed in the solvent. The surfactant may stabilise the emulsion. The combining may comprise adding the solution to the mixture or adding the mixture to the solution. It may be accompanied by agitation, optionally vigorous agitation. It may be accompanied for example by stirring, shaking, swirling, sonicating or more than one of these.

allowing the colloidal silica in the dispersed phase to form the porous particles having the species in pores thereof: this may comprise allowing sufficient time for formation of the porous particles. This may be accompanied with suitable continued agitation as described above. The suitable time will depend on the precise nature of the emulsion. It may be for example about 1 to about 12 hours, or about 1 to 6, 1 to 3, 3 to 12, 6 to 12 or 3 to 6 hours, e.g. about 1, 2, 3, 4, 5, 6, 7, 8, 9, 10, 11 or 12 hours. In some cases, particularly those in which the pH has not been previously adjusted, this step may comprise adjusting the pH of the mixture. Target pHs and suitable reagents for achieving this are similar to those described earlier for pH adjustment. It should be noted that the particles form very rapidly, typically in seconds, not hours, regardless of the pH. The reason for leaving the emulsion to age for the times described above is to ensure that the particles have sufficiently crosslinked to be stable to the washing process. Freshly formed bulk gels are generally easy to redisperse, compared with gels which are have been aged for several hours, which are in general difficult to redisperse.

As described above, pH may be adjusted down at one or more stages of the process of making the porous particles. This may facilitate or accelerate formation of the particles by facilitating or accelerating aggregation of the primary silica colloidal particles to form the particles.

Fully drying the particles may reduce the rate of release of the species when exposed to the trigger condition and/or may adversely affect the species (e.g. it may lead to at least partial denaturation of an encapsulated enzyme). Thus the method may be such that it does not comprise drying the porous particles. In this context, not drying refers to not removing all moisture from the particles. Thus the method may be such that an aqueous liquid remains in the pores of the porous particles. The method may comprise removing solvent, e.g. organic or non-polar solvent, from the particles. This may comprise evaporating the solvent, e.g. in a gentle stream of air or other suitable gas, preferably under conditions under which the aqueous liquid in the pores does not evaporate to a substantial degree.

The mixture described in the step of providing the dispersion may additionally comprise a protectant for protecting the species from degradation or denaturation. The protectant may comprise calcium ions. Calcium ions may be useful in preventing unfolding of proteins, and consequently in protecting the proteins from denaturation. In some instances calcium may be removed from the protein prior to the preparation of the porous particles, and therefore it may be an advantage to add it or some other protectant. This may be added to the mixture prior to formation of the emulsion, or it may be added to the colloidal silica and/or to the species prior to formation of the mixture or it may be added to the emulsion prior to or during formation of the porous particles. In some instances the protectant may be added with an acid when reducing the pH.

In summary, the present invention employs a similar synthesis and similar porous particles as WO2006/066317. Triggered release of an encapsulated species such as an enzyme has been achieved upon dilution by reversing the colloidal gelation (i.e. by disintegration of the colloidal gel). Encapsulation inside the porous silica particles provides preservation of enzymatic activity in detergents. This feature provides substantial market potential as it is currently achieved through specific stabilization and boron additives which are undesirable. More generally the present invention provides a generic method, i.e. physical entrapment which may be applied to other applications using a dilution trigger (e.g. enzyme in tooth paste), oral health supplements (Co enzyme Q10) etc., or other trigger as appropriate.

EXAMPLES

Described herein are experiments conducted with ovalbumin and subtilisin encapsulated in silica particles. Ovalbumin was used because it has a very similar molecular weight (44 kDa) and charge (pI about 4.5-4.9) to a commonly used laundry enzyme α-amylase (45 kDa, pI about 4.6-5.2). Amylase catalyses the breakdown of starch-based stains, whereas subtilisin (a protease with molecular weight of 27 kDa and pI about 9.4) aids in the break-down of protein-based stains. The focus was on achieving triggered release on dilution with water, and on maintaining activity of subtilisin encapsulated in silica particles.

Sample Synthesis

The general method of synthesis is

Reduce pH of colloidal silica (e.g. Bindzil® 30/360 or 15/500) to a suitable pH (typically 7-9) by addition of 1M HCl Dissolve active in 1.25 mL of Bindzil® at reduced pH Add silica/active solution to 35 mL of 1:5-1:10 (wt) Span20:non-polar solvent (eg kerosene, paraffin oil) solution with stirring.

After stirring for several hours, centrifuge solution to sediment particles

Wash with non-polar solvent (eg cyclohexane)

A series of samples made using various silica precursors and sample conditions were trialled. Faster release on dilution was observed when the pH synthesis was dropped to lower pH values (pH about 7-8), and paraffin oil was used instead of kerosene to reduce the particle size. Details of synthetic procedures for specific samples are given below:

a) Ovalbumin Encapsulation (Sample A)

9 g of Span 20 was dissolved in 60 mL of paraffin oil by stirring for 30 minutes.

5 mL of Bindzil® 30/360 was reduced to pH=7.5 by addition of 625 microlitres of 1M HCl.

149 mg of ovalbumin was dissolved in 2.5 mL of the pH 7.5 Bindzil® solution, by stirring for 10 minutes.

1.25 mL of the ovalbumin/Bindzil® solution was added to 34 ml of the Span20/paraffin oil solution with stirring.

0.5 mL of water at pH=9 was added 60 microlitres of $Ca^{2+}$ solution (600 mg $mL^{-1}$ $CaCl_2$ in 1M HCl) was added After stirring for about 4 hours, the solution was transferred to a falcon tube, and centrifuged for 10 minutes at 4000 rpm Cyclohexane was added to the tube, and stirred for 20 minutes, followed by centrifuging at 3000 rpm for 5 mins.

The solid was then washed three times with cyclohexane, centrifuging for 5 minutes at 3000 rpm to remove the supernatant each time.

Finally, the solid was dried overnight under a gentle flow of air

The mass was recorded the next day as 708.7 mg

Figure 6:
FIG. 6 is an optical micrograph of sample A, as described in the Examples [Scale bar=10 μm]

Optical microscopy (see FIG. 6) revealed mostly spherical particles.

The ovalbumin loading was subsequently determined by bicinchoninic acid (BCA) assay as 11.97% b) Subtilisin Encapsulation 3 g of Span 20 was dissolved in 20 mL of paraffin oil by stirring for 30 minutes.

1 mL of Bindzil® 30/360 was reduced to pH =8 by addition of 108 microlitres of 1M HCl.

1.75 mL of $CaCl_2.2H_2O$ solution (25 mg $mL^{-1}$ in water) was added to the Bindzil® solution to give a concentration of about 100 mM $CaCl_2.2H_2O$.

16.6 mg of subtilisin (Sigma Subtilisin A) was dissolved in 1.0 mL of the Bindzil® solution, by stirring for several minutes.

The subtilisin/Bindzil® solution was added to the Span20/paraffin oil solution with stirring.

After stirring for about 5 hours, the solution was transferred to a falcon tube, and centrifuged for 10 minutes at 4000 rpm Cyclohexane (20 mL) was added to the tube, and stirred for 20 minutes, followed by centrifuging at 3000 rpm for 5 mins.

The supernatant was discarded and the weight of wet particles recorded as 628 mg The maximum subtilisin loading in the wet particles was calculated (assuming 100% encapsulation) as 2.6 wt %.

Release Tests

Release of Ovalbumin

Release was tested under two main conditions. The first represents storage in the detergent and was simulated by using pH=9.0 solution with added $Ca^{2+}$. Particles were added to give 5 wt % particles in solution (termed 'concentrated' release). The second release was in diluted conditions to simulate a laundry wash environment. The effective dilution used was typically ×400, although this was later extended to ×2500, which is possibly unrealistically high. The protocol evolved with time, including sampling time points. A general protocol is described below, but samples differ in the actual time points recorded.

The most significant change made to the protocol during release testing was that the dilute release was changed from the addition of dry particles to water, to dilution of wetted particles in water, as it was found that wetted particles released more slowly than dry particles added to water. This is potentially due to capillary pressure leading to the rapid disintegration of the dried particles. In addition, tap water was used for the dilute release in some cases, to more closely simulate the laundry environment.

a) Original Release Protocol

Concentrated Release

All the release samples are run in quadruplicate.

Suspend 50 mg in 1 mL of deionised water at. pH=9 with added $Ca^{2+}$ ($CaCl_2.2H_2O$). Vortex to mix and shake at ambient temperature. At time points 0.5, 5 and 24 hours, spin down and remove 50 microlitre samples from each. Vortex to remix. Freeze for analysis (standard BCA).

Dilute Release

Suspend 5 mg particles in 40 mL deionised water. Vortex to mix and shake at ambient temperature. At various time points up to 5 hours, spin down and remove 0.5 mL samples from each. Vortex to remix. Freeze samples for analysis (i.e. microBCA).

b) Modified Release Protocol

Concentrated Release

All the release samples were run in quadruplicate.

Immerse 6.25 mg particles in 125 microlitres pH 9 solution containing 3 mg $ml^{-1}$ $Ca^{2+}$ Agitate for 24 hours Remove 25 microlitre sample, add 50 microlitres to aliquot, mix thoroughly and remove 50 microlitres for assay (accounting for dilution factor when calculating results).

Dilute Release (Follows Concentrated Release)

Dilution factor=500.

Note—all release samples were run in quadruplicate, and each sample was sampled twice for additional accuracy (total number of samples=8)

Dilute 6.25 mg sample in 100 microlitres liquid remaining from concentrated release above, into 50 mL tap water.

Agitate for 30 minutes (i.e. the estimated washing cycle).

Remove 2×0.5 mL samples for micro-BCA assay.

See below for diagrammatic representation of release protocol.

Extended Dilute Release (Follows Concentrated Release but the Concentrated Solution is not Sampled in this Case)

Dilution factor=2500.

Note—all release samples were run in quadruplicate, and each sample was sampled twice for additional accuracy (total number of samples=8).

Suspend 1.00 mg of sample in 20 microlitres pH 9 solution containing 3 mg $ml^{-1}$ $Ca^{2+}$ After 24 hours agitation, dilute (without sampling) into 50 mL $H_2O$.

Agitate for 30 minutes, then remove 2×0.5 mL samples for microBCA analysis.

Figure 7:
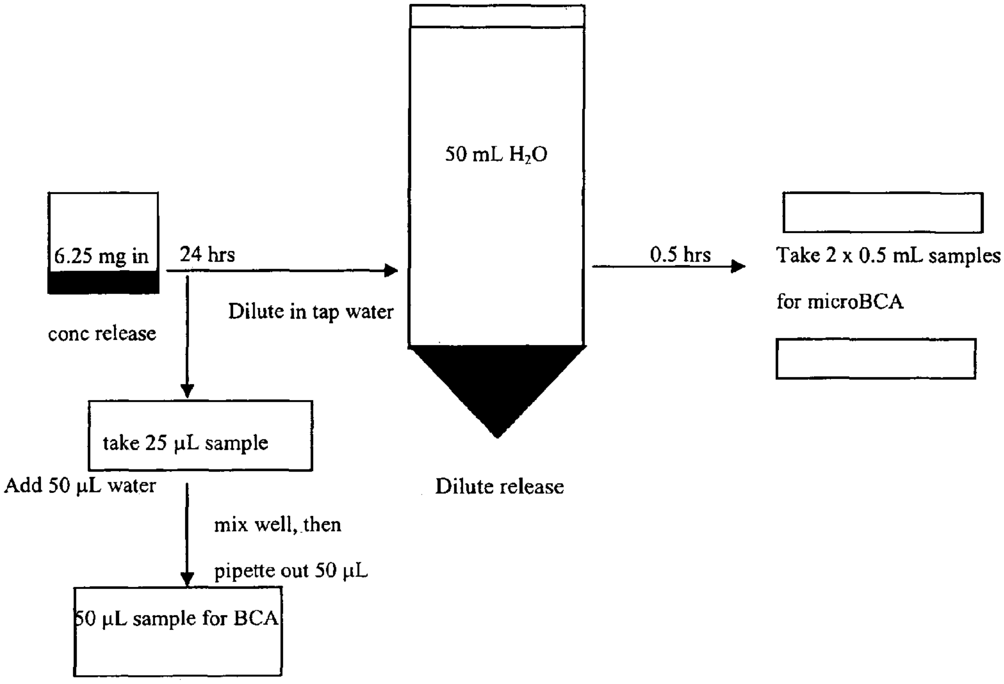
FIG. 7 is a diagrammatic representation of a release protocol of the Examples, using 500×dilution.

FIG. 7 shows a diagrammatic representation of the modified release protocol, using 500×dilution.

Release of Subtilisin

The extent of release of subtilisin from silica particles could not be quantified using a standard BCA assay as for ovalbumin, due to interference from what is thought to be a relatively small proportion of the enzyme which has been autolysed. Instead, a measure of the release into solution was obtained by measuring an activity assay. In order to estimate the concentration of subtilisin in the solution, the approximation was made that 100% of the enzyme had been encapsulated. An assay using the substrate N-succinyl-ala-ala-pro-phe-p-nitroanilide (AAPF) was used to determine the activity of the subtilisin. Subtilisin cleaves the amide bond between phenylaniline and p-nitroaniline of AAPF, producing absorption at 410 nm. The initial rate of change in absorbance at 410 nm is used as a measure of proteolytic activity. Typically absorbance values vary by up to about 0.5 absorbance units corresponding to reaction of approximately 4% of the substrate added (i.e. the substrate concentration is not limiting the rate of reaction).

The following is the method used for determining the relative enzyme activity.

- Weigh the equivalent of 150 micrograms of subtilisin into a 50 mL polypropylene centrifuge tube about 5.5 mg of undried particles—exact weight recorded)
- Add 100 mg of detergent and screw down lid
- Stand at 37° C. with slow agitation
- When required, add 45 g tap water (dilution factor=450) and vortex
- Agitate on shaker for 15 minutes
- Centrifuge for 1 minute and remove 1 mL of supernatant The mass of particles added corresponds to 1.16 wt % dry silica, and 0.15 wt % subtilisin in the detergent before dilution in tap water.

At time zero, two subtilisin samples were weighed into tubes and detergent added as above. In addition, as a control for each time point, 20 microlitres of a freshly prepared 7.5 mg/mL solution of subtilisin was added to two tubes and detergent added as above. All samples were stored under gentle agitation at 37° C. One sample (and control) was removed after about 10 minutes, and the second sample (and control) after 24 hours. The enzyme activity for each sample was determined using the following assay procedure:

- Equilibrate the UV/Vis spectrometer sample compartment to 25° C.
- Equilibrate the buffer (100 mM Tris HCl (pH 8.6) with 10 mM $CaCl_2.2H_2O$) and AAPF solution (160 mM in dry DMSO) to 25° C.
- Add 1 mL of buffer to microcuvette
- Add 10 microlitres of AAPF solution to buffer and stir to mix
- Stand cuvette at 25° C. to equilibrate for 2 mins
- Transfer cuvette to UV/Vis spectrometer
- Start 5 min collection of UV/Vis absorbance data at 410 nm every 10 seconds
- After 1 min, remove cuvette and add 10 microlitres of supernatant solution and mix quickly
- Return cuvette to UV/Vis for remaining measurements (about 4 mins)

Each enzyme assay was conducted in triplicate. The activity is defined as the slope of the absorbance curve against time (in absorbance units per minute), and is determined by linear regression of the data collected over the 4 minutes after the supernatant addition (containing released subtilisin).

Release Results

Release of Ovalbumin

Figure 8:
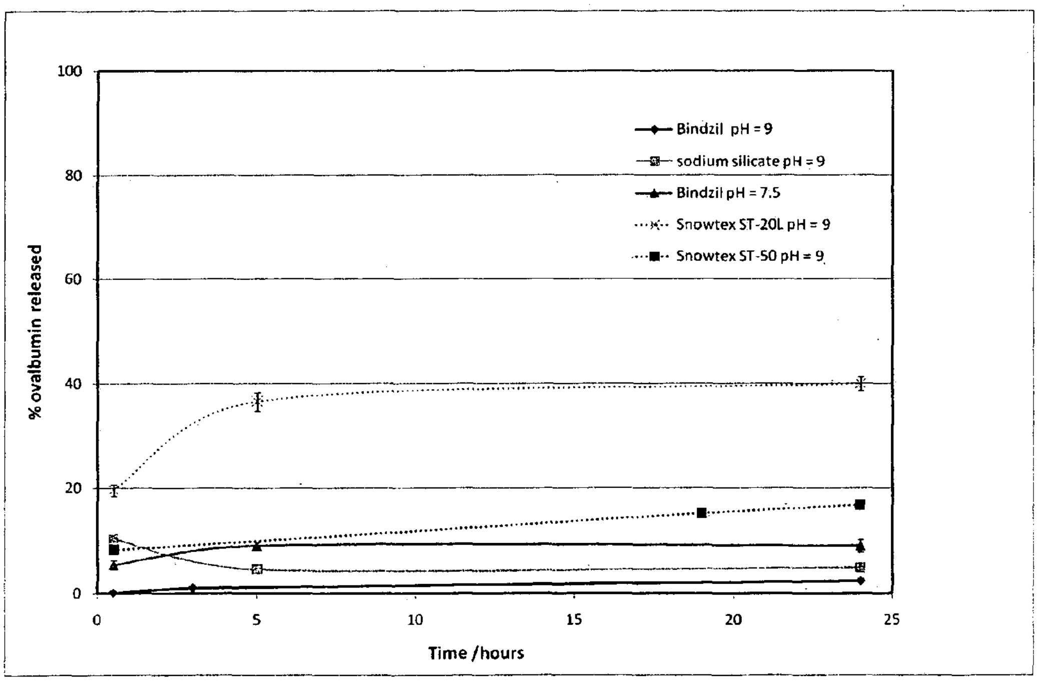
FIG. 8 is a graph showing release of ovalbumin from silica particles in concentrated conditions.
Figure 9:
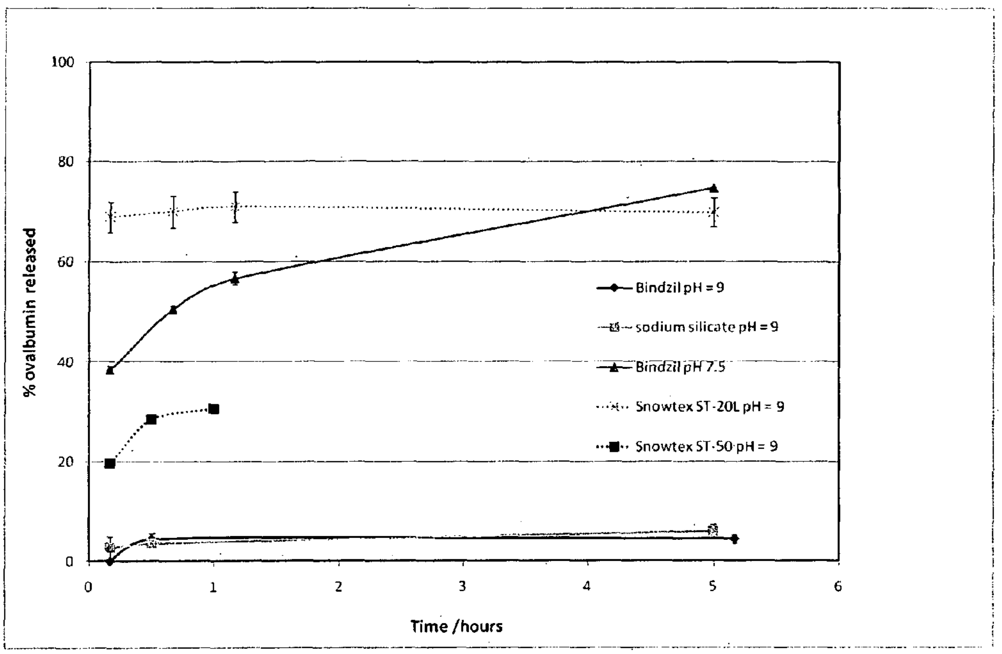
FIG. 9 is a graph showing release of ovalbumin from silica particles in diluted conditions (dilution factor=400)

A number of silica precursors were tested, including sodium silicate at pH=9, Bindzil® 30/360 reduced to pH=9 and 7.5, Snowtex® 20 L and Snowtex® 50T. It is known from previous work that reducing the pH of the colloidal silica before addition to the emulsion results In larger pores, and hence potentially faster release or disaggregation. Thus the rate of release from samples made using Bindzil® reduced to pH 7.5 would be expected to be greater compared with samples made using Bindzil® reduced to pH 9. Snowtex® ST-20 L and. ST-50 colloidal silica consist of dispersions containing primary particles of size 40-50 nm and 20-30 nm respectively, and thus should show faster release than particles made from Bindzil® which consists of primary particles about 9 nm. The results of release tests of ovalbumin-doped samples in concentrated conditions (5 wt % particles) and diluted by a factor of 400 in deionised water are shown in FIGS. 8 and 9 respectively.

Bindzil® 30/360 reduced to pH 8 or below was found to be the optimum precursor for release of ovalbumin (ie relatively low release (<10%) in concentrated conditions and reasonably rapid release in dilute conditions), as long as care was taken to minimise the particle size (use ultrasonics when adding precursor to emulsion, or use paraffin oil as solvent).

Figure 10:
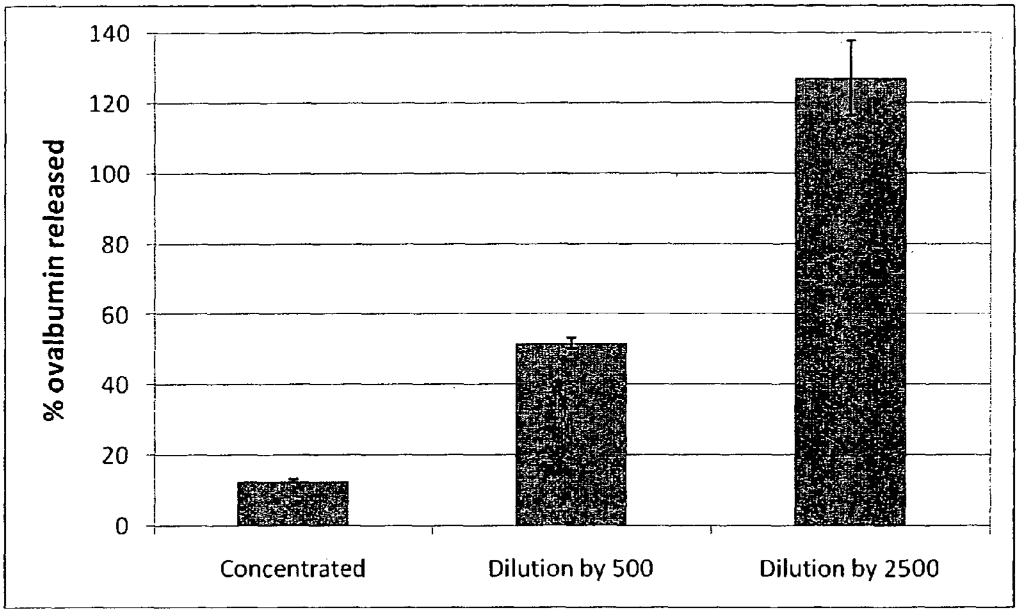
FIG. 10 is a graph showing release of ovalbumin from silica particles, under concentrated conditions (5 wt % particles in solution at pH=9.0, with 3 mg/mL $CaCl_2$) and diluted×500 and×2500 in tap water.
Figure 11:
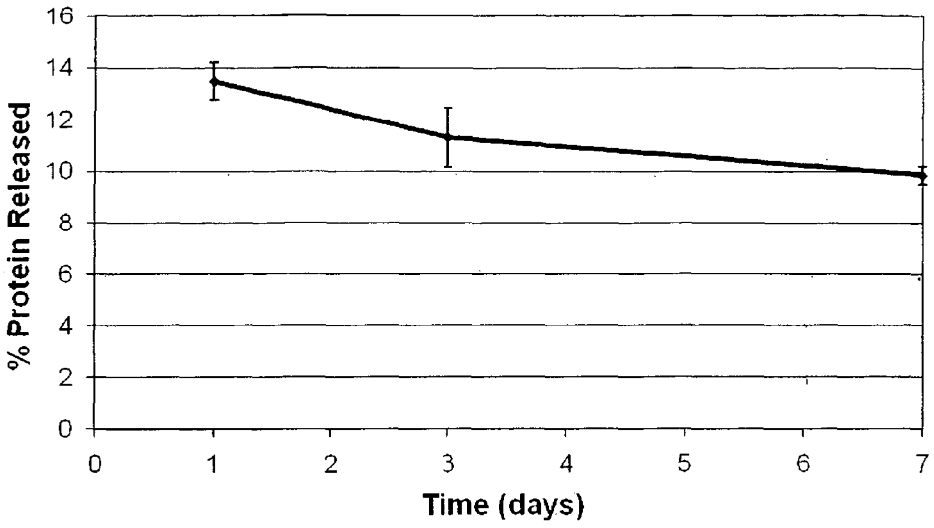
FIG. 11 is a graph showing release of ovalbumin from silica particles under concentrated conditions, after 1, 3 and 7 days.

Ovalbumin release results of Sample A (see above for synthesis details) are shown in FIG. 10. Release was measured using the modified protocol, with tap water used to dilute the concentrated solution. It was found that use of tap water resulted in significantly greater release in dilute conditions, compared with distilled water. Concentrations of 3 mg/mL $CaCl_2$ were used in the concentrated conditions as release (typically about 10-20%) was lower than when 1 mg/mL $CaCl_2$ was used, which gave concentrated release about 25-35%. However, it is expected that use of detergent rather than simply pH=9 solution with added calcium, would result in lower releases. The concentrated release results shown in FIGS. 8 and 10 correspond to 24 hours immersed in the solution before sampling. A longer term test was conducted, with results shown in FIG. 11. It is possible that the protein is either increasingly sticking to the particles with time, or is being degraded to some extent in the solution at pH=9. Nevertheless, it would appear that the protein release which does occur, happens rapidly (≤1 day) on immersion, and does not increase significantly with time.

Release of Subtilisin

The relative activities of encapsulated subtilisin and unencapsulated control samples on day 0 and day 1 are listed in Table 1. Note that the enzyme concentrations correspond to the nominal concentration in the tap water diluted solution, assuming 100% encapsulation of enzyme in the particles.

TABLE 1

Subtilisin activities determined for tap-water diluted detergent solutions containing encapsulated and free subtilisin respectively.

| | Encapsulated subtilisin | | Unencapsulated subtilisin | |
|---|---|---|---|---|
| | Day 0 | Day 1 | Day 0 | Day 1 |
| Enzyme concentration μg/mL) | 3.16 | 3.34 | 3.61 | 3.61 |
| Average activity (A.U./min) | 0.254 ± 0.011 | 0.309 ± 0.005 | 0.303 ± 0.003 | 0.320 ± 0.014 |
| Normalised activity (A.U./min per μg per mL) | 0.081 ± 0.008 | 0.093 ± 0.006 | 0.084 ± 0.004 | 0.088 ± 0.008 |

Comparison of the normalised enzyme activities determined on day 0 and day 1 suggest that there is little difference in activity between the encapsulated and unencapsulated subtilisin. This suggests that both the encapsulation efficiency and the extent of release of enzyme were close to 100%.

Conclusions

Ovalbumin-doped particles made using Bindzil® 30/360 reduced to pH=7.5 (Sample A) were found to show

- limited release of ovalbumin (typically 10-20%) after 24 hours at 5 wt % in pH=9 solution with added $CaCl_2$ (simulated detergent conditions)
- little or no additional release in concentrated conditions with extended standing
- rapid release on dilution ×500 in tap water
- more extensive release on increased dilution (up to ×2500)

Subtilisin-doped particles made using Bindzil® 30/360 reduced to pH=8 and adjusted to 100 mM $CaCl_2.2H_2O$ (Sample B) were found to have similar activity to control solutions. This indicates almost quantitative encapsulation and release of enzyme under the conditions employed.

Further Examples

The following examples demonstrate the application of the particles described in the examples above to delivery of laundry enzymes.

General Method for Determining Storage Stability of Encapsulated Protease

Samples of enzymes were stored in various media, contained in 50 mL polypropylene centrifuge tubes known to have low protein uptake on the container walls. This enabled rapid dilution and separation from residual solid by centrifugation, in order to conduct a protease activity assay of the released enzyme. Samples were stored under gentle agitation for varying periods at 37° C. to accelerate the deterioration encountered on storage at ambient temperature. At time zero, equal numbers of encapsulated and control samples (i.e. freshly dissolved enzyme) were prepared by suspending weighed amounts of material in 0.1 mL of storage media. The concentration of enzyme used was 0.12-0.15 wt %, somewhat above the typical concentration of 0.05-0.1 wt % enzymes in liquid laundry detergents, but necessary to improve the accuracy of the enzyme assay.

An activity determination at each time point thus consisted of the following steps:

- addition of 45 g of tap water to the sample;
- vortexing to thoroughly mix the enzyme/media suspension into the tap water;
- agitation of the sample (shaker table) for 15 minutes;
- one minute centrifuge using 2500×g RCF to spin down any residual solid;
- 1 mL aliquot of supernatant taken for activity testing.

In the case of the control samples (no particles), the centrifuge step was omitted. It should be noted that the dilution factor of 450 used here is somewhat lower than the typical dilution factor of 500-1000, in order to keep the enzyme concentration relatively higher in the tap water. This was necessary to increase the signal-to-noise ratio in the enzyme assay.

An assay using the substrate N-succinyl-ala-ala-pro-phe-p-nitroanilide (AAPF) was used to determine the activity of the protease. Protease cleaves the amide bond between phenylaniline and p-nitroaniline of AAPF, producing absorption at 410 nm. The initial rate of change in absorbance at 410 nm is used as a measure of proteolytic activity. Typically absorbance values vary by up to about 0.5 absorbance units corresponding to reaction of approximately 4% of the substrate added (i.e. the substrate concentration is not limiting the rate of reaction). The enzyme activity for each sample was determined using the following assay procedure:

- equilibrate the UV/Vis spectrometer sample compartment to 25° C.;
- equilibrate the buffer (100 mM Tris HCl (pH 8.6) with 10 mM $CaCl_2.2H_2O$) and AAPF solution (160mM in dry DMSO) to 25° C.;
- add 1 mL of buffer to microcuvette;
- add 10 μL of AAPF solution to buffer and mix well;
- transfer cuvette to UV/Vis spectrometer to equilibrate at 25° C. for 2 mins;
- zero the absorbance reading;
- start 4 min reading of UV/Vis absorbance at 410 nm every 10 seconds;
- after several measurements, remove cuvette and add 10 μL of supernatant solution and mix well;
- return cuvette to UV/Vis spectrometer for the remaining measurements Each enzyme assay was conducted in triplicate. The activity is defined as the slope of the absorbance curve against time (in absorbance units per minute), and is determined by linear regression of the data collected after the supernatant addition (containing released protease). The data is normalised for concentration of protease (calculated assuming 100% encapsulation) and expressed as a fraction of the control activity at time zero.

Example 1

Protection of Subtilisin in PBS and Release Kinetics

Particle Synthesis

The pH of 30 wt % colloidal silica (Bindzil 30/360, 1.0 mL) was reduced by addition of HCl (1M, 0.091 mL), and the sample diluted with 1.75 mL of $CaCl_2.2H_2O$ solution (25 mg/mL) which contained 2 wt % carboxymethylcellulose. 8 mg of protease (subtilisin) was dissolved in 1.0 mL of the diluted silica solution, and added with vigorous stirring to 20 g of a paraffin oil (heavy grade) mixture containing 15 wt % sorbitan monolaurate. After stirring for 2.5 hours, the paraffin solution was centrifuged (2500×g RCF, ten minutes) to isolate the solid, which was washed with cyclohexane (20 mL) and then cyclohexanone (5 mL) to remove excess oil and surfactant by centrifuging as above. The relative amounts of silica and enzyme added in the synthesis corresponds to a mass ratio of 1:15.9 enzyme: dry silica.

Stability Study

Figure 12:
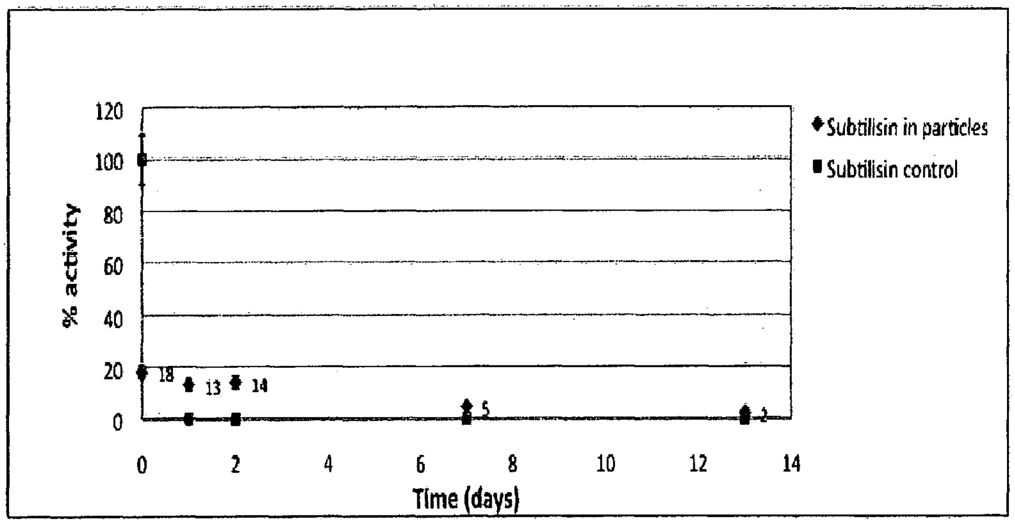
FIG. 12 shows a graph illustrating activity of protease (subtilisin)—encapsulated and free—after storage in PBS, as a percentage of the normalised control activity at time zero.
Figure 13:
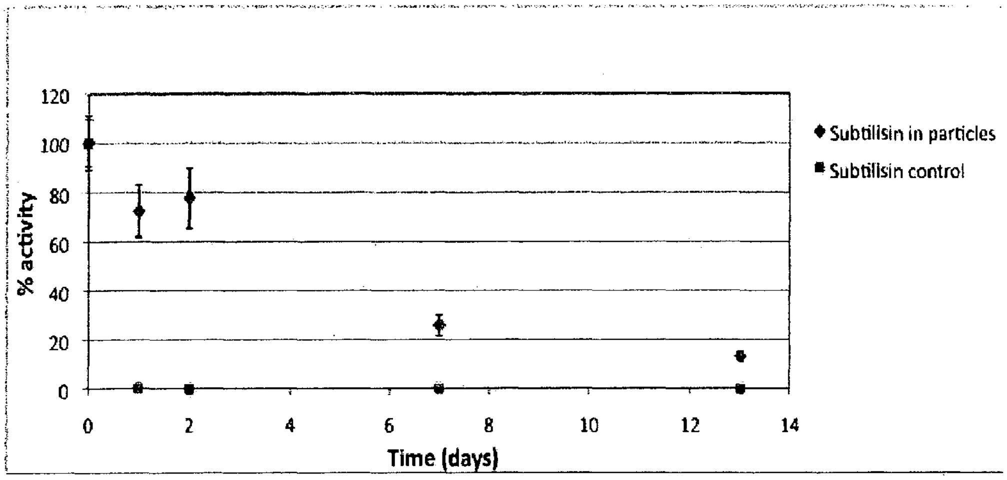
FIG. 13 shows a graph illustrating activity of protease (subtilisin)—encapsulated and free—after storage in PBS, as a percentage of the maximum activity.

Samples were suspended in 0.1 mL of phosphate buffered saline (PBS, 0.01M) for a stability trial. The control samples also contained an equivalent carboxymethylcellulose:enzyme ratio as expected in the particles. The results of measurements over a two week period are shown in FIGS. 12 and 13. FIG. 13 shows the activities in absolute % of the normalised control activity, and assumes 100% encapsulation. FIG. 13 shows data ratioed to the maximum activity of the sample, which more clearly shows the relative change in activity with time. The activity of the unencapsulated enzyme control was reduced to zero after 24 hours in PBS. This rapid drop in activity was due to autolysis of the protease.

The activity of the encapsulated enzyme was relatively low compared with that of the control. There are several possible reasons for this. Firstly, the enzyme is assumed to be fully encapsulated, with no loss in the supernatant. Secondly, the enzyme is assumed to be completely unaffected by the encapsulation process. Thirdly, the enzyme is assumed to be fully released on dilution with tap water. A failure in any of these assumptions will result in a relatively lower activity than expected.

FIG. 13 shows the trend in activity in the encapsulated enzyme with time. Rather than being reduced to zero, the activity after storage for one day was still 75% of the original activity. Similar activity was observed on day 2. After one week, the activity has been reduced to 26% of the original activity and to 13% after two weeks. It is clear that encapsulation in silica significantly stabilises the enzyme against self-destruction, which would otherwise result in zero activity after one day.

Release Kinetics Investigation

Figure 14:
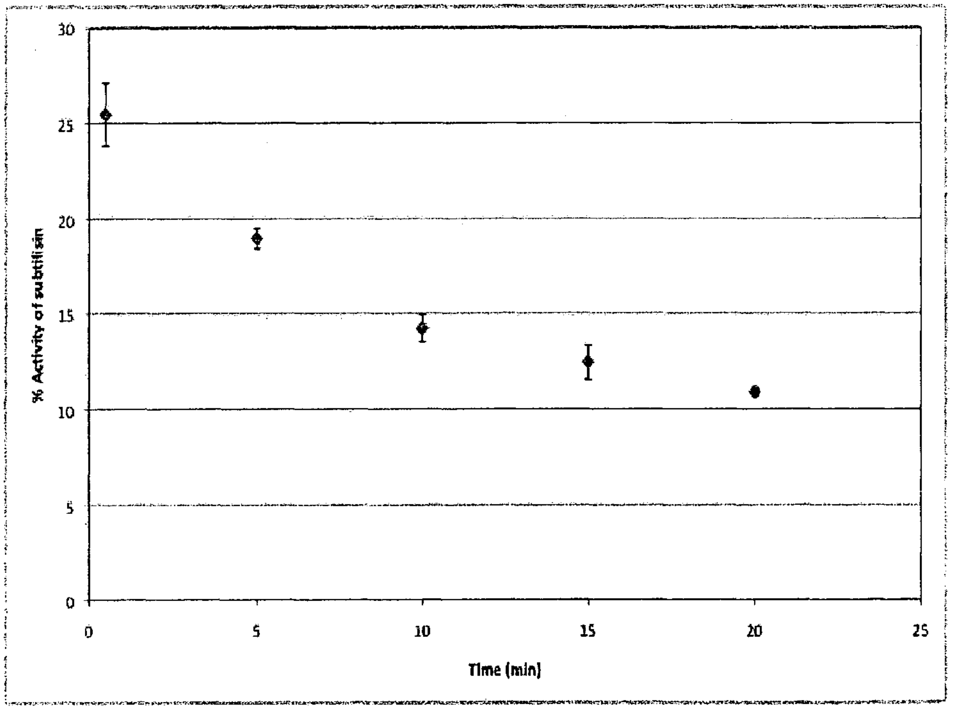
FIG. 14 shows a graph illustrating subtilisin activity after release into tap water (mean±s.e.m, n=3)

In order to determine the release profile of subtilisin from the particles into tap water, the release procedure was conducted slightly differently. Three samples of encapsulated subtilisin were suspended in PBS as above, and stored for two days at 37° C. Under these conditions, enzyme which has leached from the particles should have no remaining activity. Tap water was added to the first sample, but rather than waiting for 15 minutes to collect the supernatant, the sample was centrifuged and 10 μL samples taken at the following times after dilution; 0.5, 5, 10 15 and 20 minutes. The sample was revortexed and left agitating after each aliquot was taken. The activity assay was conducted immediately after extracting the 10 μL sample. This procedure was repeated for the other two samples, and the results averaged to give more statistically relevant data. The activities were normalised using the previous control data determined on day zero (taken after 15 minutes). FIG. 14 shows the change in activity with sampling time.

The observation of highest activity after 0.5 minutes release time indicates that enzyme release from the particles occurs essentially instantaneously after dilution with tap water. The decrease in activity with time is most likely due to autolysis of the enzyme in the tap water. Very little sample-to-sample variation was observed, indicating that the encapsulated enzyme material was homogeneous, and the release behaviour was reproducible.

Example 2

Protection of Subtilisin in Synthetic Detergent

Particle Synthesis

Particles with encapsulated subtilisin were synthesised using the procedure outlined in Example 1.

Stability Study

A stimulant aqueous detergent was synthesised with the following composition:

6 wt % sodium lauryl ether sulphate,
3 wt % sodium toluene sulphonate,
2.5 wt % $C_{18}EO_2$ alcohol ethoxylate,
3 wt % $C_{13}EO_{10}$ alcohol ethoxylate,
2 wt % oleic acid,
2 wt % monopropylene glycol,
4 wt % sodium citrate dihydrate,
0.4 wt % triethanolamine,
0.5 wt % ethanol.

The mixture was adjusted to pH 8.5 using 1M NaOH.

Encapsulated and control samples were aged in 0.1 mL of the above detergent using the standard conditions. The results over a two week period are shown in FIGS. 15 and 16.

Figure 15:
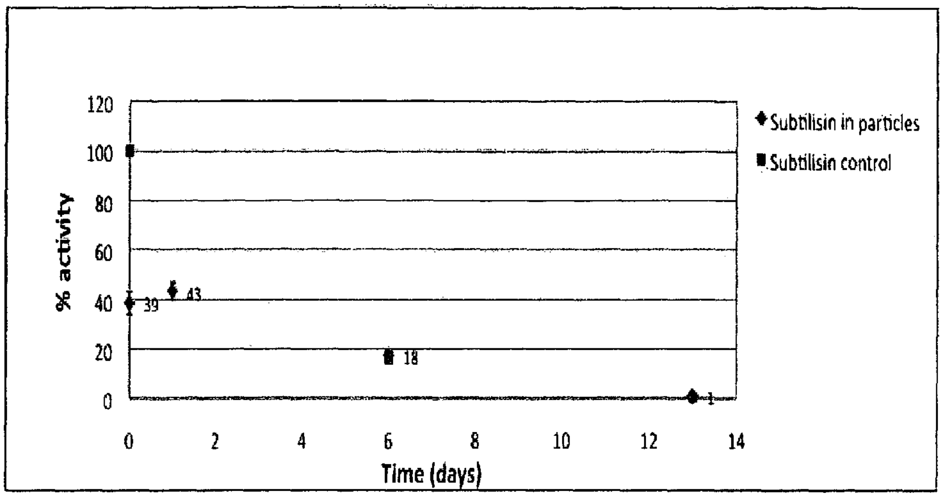
FIG. 15 shows a graph illustrating activity of protease (subtilisin)—encapsulated and free—after storage in synthetic detergent, as a percentage of the normalised control activity at time zero.
Figure 16:
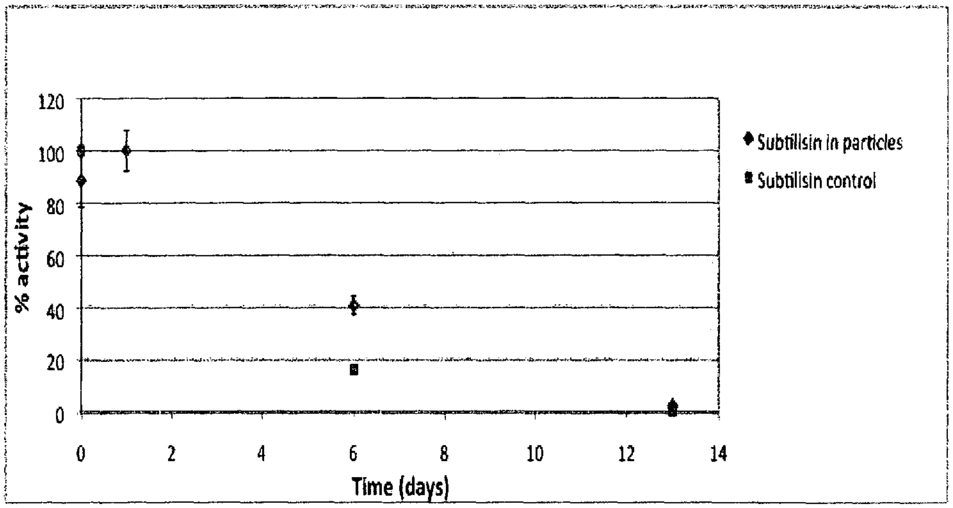
FIG. 16 shows a graph illustrating activity of protease (subtilisin)—encapsulated and free—after storage in synthetic detergent, as a percentage of the maximum activity.

As for the previous sample, FIG. 15 contains the activities in absolute % of the normalised control activity, and assumes 100% encapsulation. FIG. 16 contains data ratioed to the maximum activity of the sample. An initial activity of about 40% is somewhat higher than in the first example and could indicate some sample-to-sample variation. However, the treed with time was similar. After 6 days, the activity has been reduced to 40% of the maximum activity (compared with 26% after 7 days in PBS), but almost reduced to zero after two weeks.

Example 3

Protection of Industrial Subtilisin in Synthetic Detergent

Particle Synthesis

An industrial subtilisin was trialled for comparison with the research grade protease. Synthesis of particles with encapsulated subtilisin was as described above for Example 1, but the addition of carboxymethylcellulose was omitted and 15 mg of subtilisin was used in the preparation.

Stability Study

Figure 17:
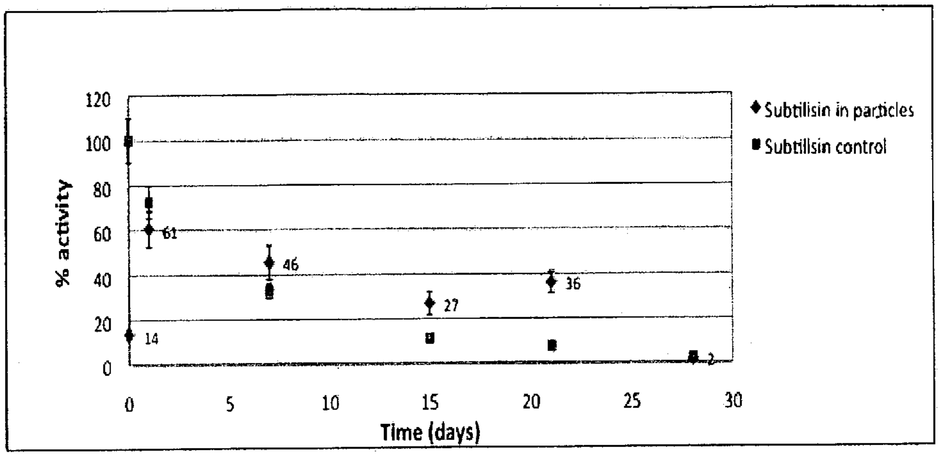
FIG. 17 shows a graph illustrating activity of industrial subtilisin after storage in synthetic detergent, as a percentage of the normalised control activity at time zero.
Figure 18:
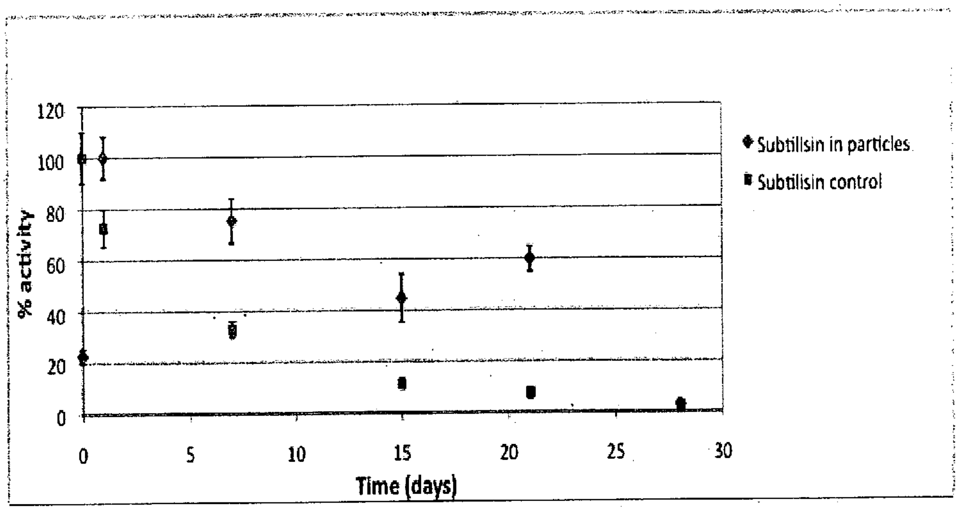
FIG. 18 shows a graph illustrating activity of industrial subtilisin after storage in synthetic detergent, as a percentage of the maximum activity.

Encapsulated and control samples were aged in 0.1 mL of the synthetic detergent using the standard conditions. The results over a four week period are shown in FIGS. 17 and 18. It is interesting to note again the relatively low activity (14%) on day 0 compared with day 1 (61%) for the encapsulated sample. There appears to be a temporary 'recovery period' after the encapsulation process and could indicate a possible structural re-adjustment of the enzyme during this time. Comparison of the encapsulated and control activities (as % of maximum) showed a clear enhancement due to the protective effect of the particle matrix. The activity after one week (75% of maximum activity) was considerably higher than for the research grade subtilisin (40% of maximum activity after 6 days). After two and three weeks storage the activities were found to be 45 and 60% respectively (again, some sample variation suspected), compared with no activity for the research subtilisin. However, at week four, the activity was almost zero.

Example 4

Protection of Industrial Subtilisin in Synthetic Detergent—Modified Synthesis Particle Synthesis The effective dilution of the colloidal silica precursor in the particle synthesis of Example 1 was reduced to determine any difference in ensuing activity of the encapsulated enzyme. As for Example 3, carboxymethylcellulose was omitted from the synthesis, and 15 mg of subtilisin was used. A similar procedure to Example 1 was used, except that the volume of $CaCl_2.2H_2O$ solution (25 mg/mL) used to dilute the acidified silica was reduced from 1.75 mL to 1.25 mL. This corresponds to an increase in the enzyme: dry silica mass ratio, from 1:8.5 to 1:10.2, due to the reduced dilution of silica with calcium solution.

Stability Study

Figure 19:
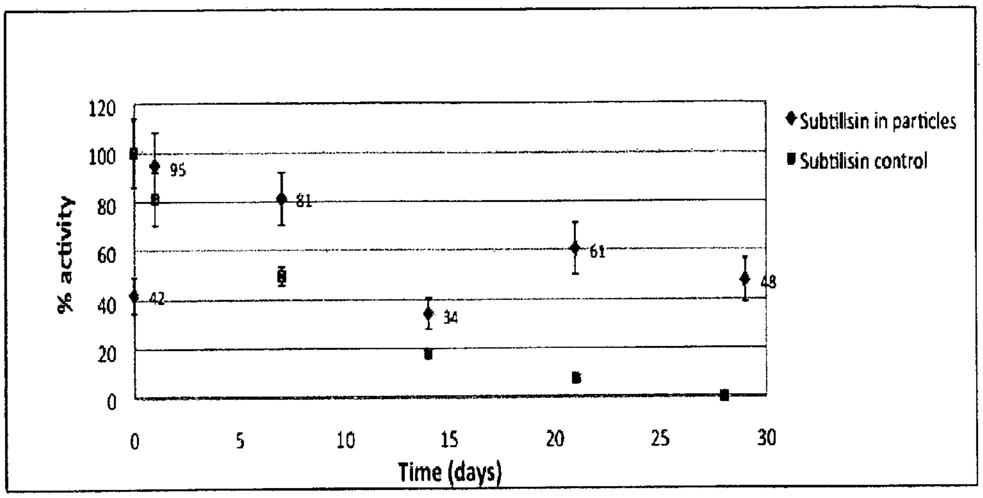
FIG. 19 shows a graph illustrating activity of industrial subtilisin after storage in synthetic detergent, as a percentage of the normalised control activity at time zero.
Figure 20:
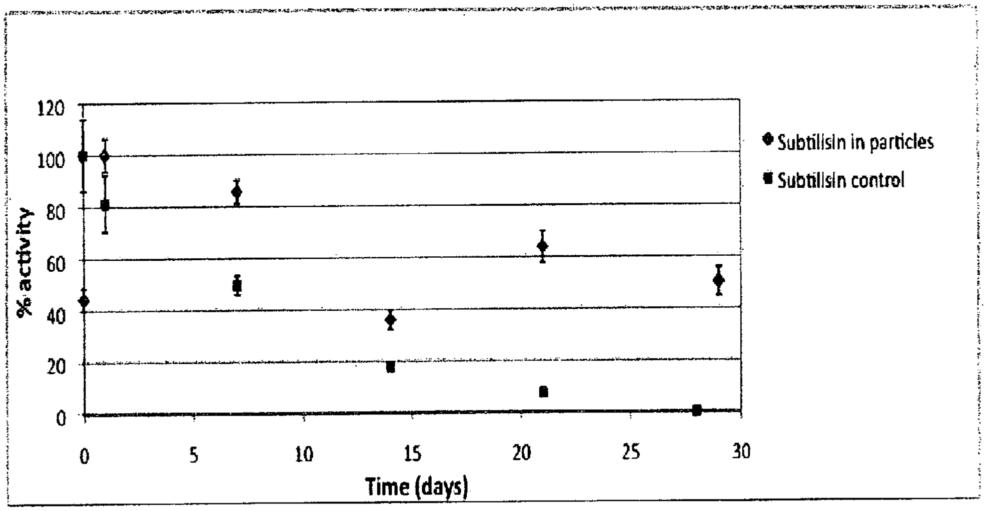
FIG. 20 shows a graph illustrating activity of industrial subtilisin after storage in synthetic detergent, as % of the maximum activity.

Encapsulated and control samples were aged in 0.1 mL of the synthetic detergent using the standard conditions. The results over a four week period are shown in FIGS. 19 and 20. The absolute activities of the encapsulated enzyme are considerably higher in comparison with the previous example. The reason for this is thought to be higher encapsulation efficiency with reduced dilution of the silica precursor. Some water is incorporated in the particle gel matrix, but excess water is removed in the supernatant during isolation of the solid, and results in some loss of enzyme. Although the encapsulation efficiency is assumed to be 100% for the normalisation procedure, in reality, it is likely to be considerably less than this: However, an activity of 95% in the present example suggests that the encapsulation efficiency is close to 100% when the amount of excess water in the system is reduced. The stability with time is also increased, with about 50% remaining activity after one month, compared with almost no activity in the initial sample.

Example 5

Alternative Synthesis—Effect of Particle Size

Particle Synthesis

The particles used in the previous examples have been synthesised using a sorbitan monolaurate/paraffin oil surfactant mixture. An alternative surfactant/oil combination which gives a suitable emulsion with the colloidal silica mixture is dioctylsulfosuccinate sodium salt in vegetable oil. One unknown factor was the extent to which a less viscous solvent would affect the particle size, and thus, potentially, the release kinetics and observed enzyme activity. In addition to the pH (typically about 8), which influences the pore size, another factor which it was thought might influence the release kinetics, and hence the observed enzyme activity, is the average particle size. As indicated in FIG. 14, the release of the encapsulated enzyme is very rapid when the particle size is small. The particle size is at least in part controlled by size of the emulsion droplets, and hence by the surfactant/solvent properties, and by the amount of energy supplied to the system during the synthetic procedure. In the previous examples, the particle size has been minimised by the use of heavy grade paraffin oil. In general, the average particle size is inversely dependent on the solvent viscosity. In the present example, a less viscous solvent (and different surfactant) were employed, and shear mixing used in one set of particles in order to further modify the average particle size.

The pH of 30 wt % colloidal silica (Bindzil 30/360, 1.0 mL) was reduced by addition of HCl (1M, 0.096 mL), and the sample diluted with 1.25 mL of $CaCl_2.2H_2O$ solution (25 mg/mL). 16 mg of industrial subtilisin was dissolved in 1.0 mL of the diluted silica solution, and added to 45 mL of 165 mM dioctyl sulfosuccinate sodium salt in vegetable oil. For both sets of particles, vigorous stirring was employed, but the second sample was shear-mixed at 24,000 rpm for 30 seconds prior to and following addition of the colloidal silica/enzyme precursor to the surfactant solution. After stirring for 2.5 hours, the emulsions were centrifuged (2500×g RCF, ten minutes) to isolate the solid, which was washed with cyclohexane (20 mL) and then cyclohexanone (5 mL) to remove excess oil and surfactant by centrifuging as above. The weight of the solids obtained were about 500 mg, corresponding to 10 wt % loading of subtilisin on a dry silica basis (assuming 100% encapsulation of the enzyme).

Particle Size Distribution

Figure 21:
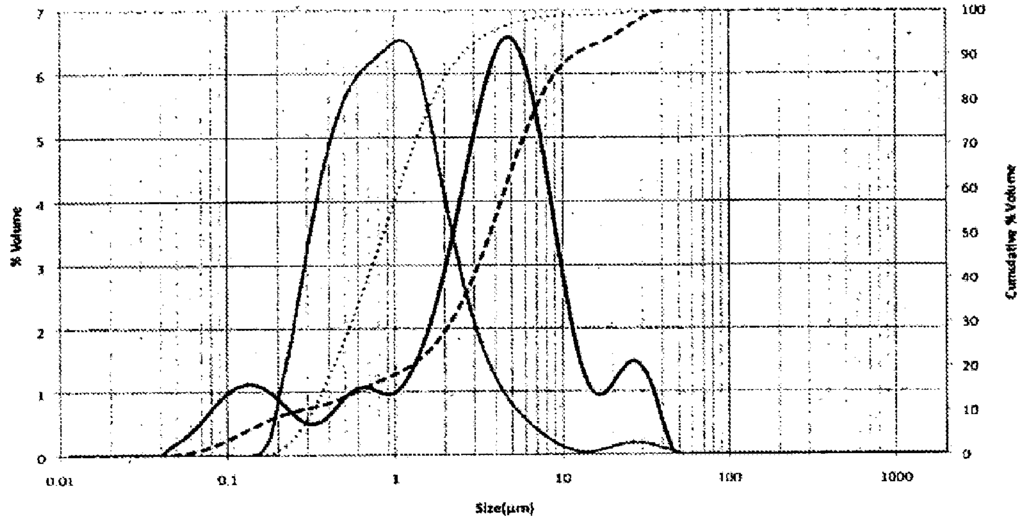
FIG. 21 shows particle size distributions of samples made using AOT/vegetable oil (-=stirred only (black line), -=shear-mixed (grey line)). The dotted lines correspond to the cumulative distributions in each case.

The particle size distributions of the two samples were determined by light scattering (Malvern Mastersizer). To avoid rapid disintegration of the particles on addition to the sample bath, ethanol was used as the dispersant instead of water. The particle size distributions of the two samples are shown in FIG. 21. Both samples have a broad size distribution, ranging from about 0.05 to 40 μm. The average ($d_{0.5}$) sizes for the stirred and sheared samples are 3.7 and 0.9 μm, respectively. The particle size distributions are plotted in FIG. 21, the dotted lines being the corresponding cumulative size distributions (red=stirred, blue=shear-mixed).

It is clear that employing shear-mixing for a short period of time before and after addition of the silica precursor to the surfactant solution (about 1 minute in total) results in significant narrowing of the particle size distribution.

Enzyme Activity and Stability Study

Figure 22:
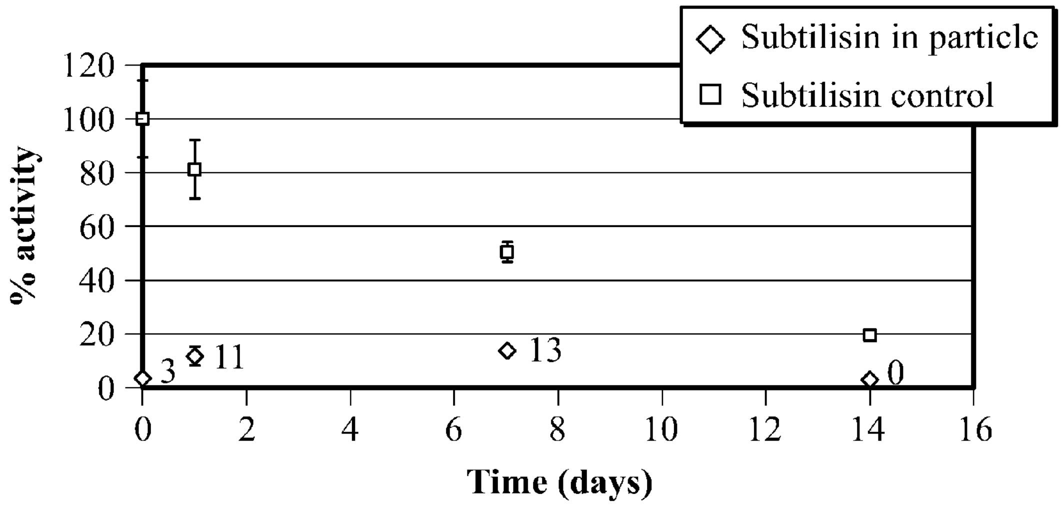
FIG. 22 shows a graph illustrating activity of industrial subtilisin after storage in synthetic detergent, as a percentage of the normalised control activity at time zero, in which the emulsion was stirred only.
Figure 23:
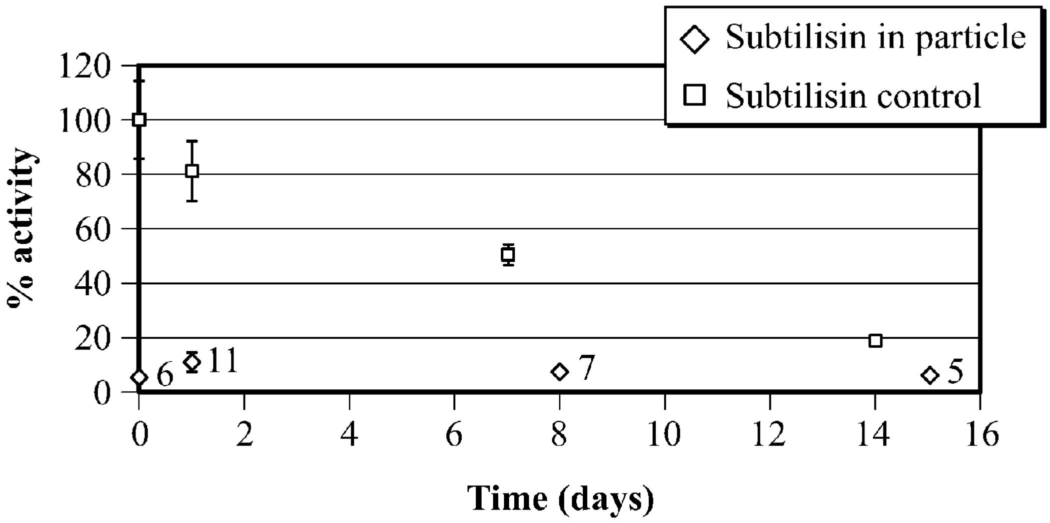
FIG. 23 shows a graph illustrating activity of industrial subtilisin after storage in synthetic detergent, as a percentage of the normalised control activity at time zero, in which the emulsion was shear-mixed.
Figure 24:
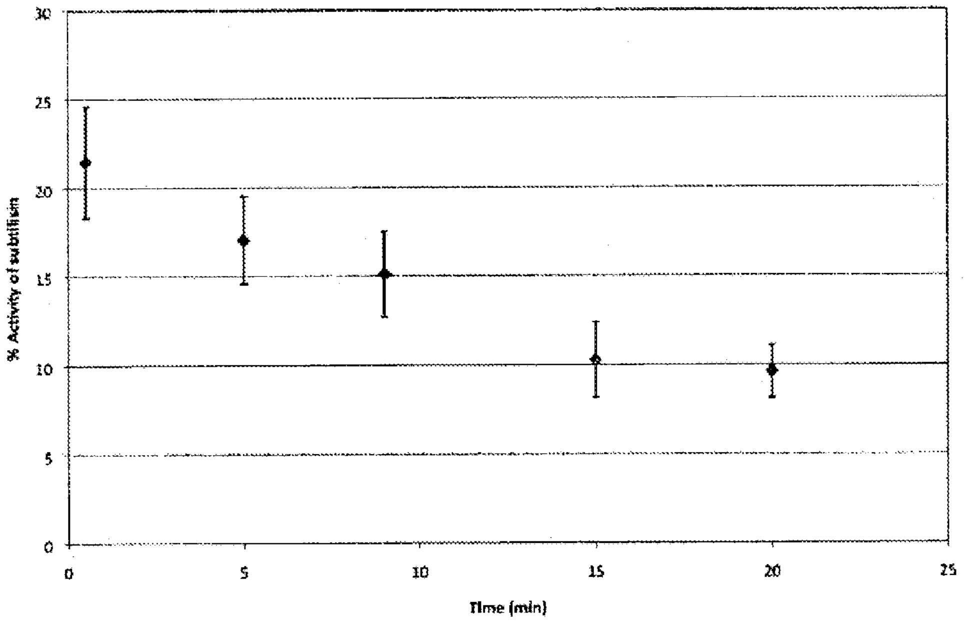
FIG. 24 shows a graph illustrating subtilisin activity after release into tap water.

Encapsulated and control samples were aged in 0.1 mL of the synthetic detergent using the standard conditions. The results (in absolution % activity units) over a two week period are shown in FIGS. 22 and 23, corresponding to the stirred and shear-mixed samples respectively. The day 0 and day 1 activities—3 and 11%, and 6 and 11%, for the stirred and shear mixed samples respectively - were significantly reduced compared with the corresponding particles made using Sorbitan monolaurate/paraffin oil (Example 4: 42 and 95%). The reason for this in not clear, but the similarity between the two samples suggests that it is not related to the particle size. Release tests were also conducted with these samples, with very similar results found to those described in Example 1, suggesting that release was very rapid (see FIG. 24). The most likely explanation for the reduced activity in these examples is that the anionic surfactant, dioctyl sulfosuccinate sodium salt, is acting to denature this particular protein. Nevertheless:use of this surfactant in vegetable oil, has resulted in very similar particles to those obtained using sorbitan monolaurate/paraffin oil, with similar release behaviour.

Summary

Silica particles showing very rapid disintegration on dilution have been doped with protease (subtilisin) for laundry applications. Tests have shown that the protease is released very rapidly on dilution with tap water (<1 minute). Although the inclusion of protease can enhance the performance of laundry detergents due to their ability to break down protein stains (blood, food etc), long-term storage of such proteases in liquid detergents is problematic due to self-autolysis of the protein, thus limiting the shelf-life of the product. A number of examples are presented where encapsulation of a protease into silica particles results in stabilisation of enzymatic activity under accelerated degradation conditions relative to the unencapsulated protein. The activity and stability of the protease can be increased by reducing excess water in the synthesis, and reducing the protein concentration in the particles.

The invention claimed is:

1. A method for delivering a species to a liquid, said method comprising:

providing porous agglomerate particles comprising a plurality of silica primary particles agglomerated so as to define pore spaces between said silica primary particles, said porous agglomerate particles further comprising a species disposed in said pore spaces, and said pore spaces of said porous agglomerate particles being sized such that said species cannot diffuse out of the pore spaces of the porous agglomerate particles; and exposing said porous agglomerate particles to a condition whereby the silica primary particles at least partially deagglomerate so that the species is released into the liquid.

2. The method of claim 1 wherein the pore spaces have a mean diameter of about 1 to about 50 nm.

3. The method of claim 1 wherein the porous agglomerate particles have a mean diameter of about 0.05 to about 500 microns.

4. The method of claim 1 wherein the silica primary particles have a mean diameter of about 5 to about 500 nm.

5. The method of claim 1 wherein the species is a biological species or a macromolecular species or a particulate species.

6. The method of claim 5 wherein the biological species is selected from the group consisting of a protein, a peptide, an enzyme, DNA, RNA, a DNA fragment and mixtures of any two or more of these.

7. The method of claim 1 wherein the condition comprises sufficient dilution in the liquid for release of the species from the porous agglomerate particles.

8. The method of claim 1 wherein the condition is selected from the group consisting of dilution, temperature, pH and combinations of any two or all of these.

9. The method of claim 1 wherein the step of providing the porous agglomerate particles comprises:

preparing a mixture of colloidal silica and the species;

combining the mixture with a solution of a surfactant in a solvent so as to form an emulsion, said emulsion comprising the mixture as a dispersed phase and the solvent as a continuous phase; and allowing the colloidal silica in the dispersed phase to form the porous agglomerate particles having the species disposed in the pore spaces thereof, wherein the mixture additionally comprises a protectant for protecting the species from degradation or denaturation.

10. The method of claim 1 wherein the release of the species from the porous agglomerate particles occurs within about 5 minutes of exposing the porous agglomerate particles to the condition.

11. The method of claim 1, wherein the species is an enzyme for use in laundry applications, said method comprising adding a dispersion of porous agglomerate particles in a detergent formulation to an aqueous liquid as a step in a process of washing laundry items, and whereby said adding is conducted so as to dilute said porous agglomerate particles in the aqueous liquid to a degree sufficient to cause at least partial deagglomeration of the porous agglomerate particles, whereupon the enzyme is rapidly released into the aqueous liquid in order to assist in said process of washing.

12. A method for delivering a species to a liquid, said method comprising:

providing porous agglomerate particles made by a process comprising preparing a mixture of colloidal silica and the species;

combining the mixture with a solution of a surfactant in a solvent so as to form an emulsion, said emulsion comprising the mixture as a dispersed phase and the solvent as a continuous phase; and allowing the colloidal silica in the dispersed phase to form the porous agglomerate particles having the species within the pore spaces thereof, said pore spaces being defined between agglomerated silica primary particles, and said pore spaces of said porous agglomerate particles being sized such that said species cannot diffuse out of the pore spaces of the porous agglomerate particles; and exposing said porous agglomerate particles to a condition whereby the silica primary particles at least partially deagglomerate so that the species is released into the liquid.

13. A method for rapidly delivering a species to a liquid, comprising:

exposing porous agglomerate particles formed from an agglomeration of silica primary particles to a condition in said liquid to cause at least partial deagglomeration of the silica primary particles, said porous agglomerate particles being made by a process comprising preparing a mixture of colloidal silica and the species;

combining the mixture with a solution of a surfactant in a solvent so as to form an emulsion, said emulsion comprising the mixture as a dispersed phase and the solvent as a continuous phase; and allowing the colloidal silica in the dispersed phase to form the porous agglomerate particles having the species within pore spaces of the porous agglomerate particles, said pore spaces being defined between agglomerated silica primary particles,and said pore spaces being sized such that said species cannot diffuse out of the pore spaces of the porous agglomerate particles.

14. A method for rapidly delivering a species to a liquid, comprising:

exposing porous agglomerate particles formed from an agglomeration of silica primary particles to a condition in said liquid to cause at least partial deagglomeration of the porous agglomerate particles, wherein said pore spaces are defined between the agglomerated silica primary particles, wherein said species is disposed in said pore spaces, and wherein said pore spaces of said agglomerate particles are sized such that said species cannot diffuse out of the pore spaces of the porous agglomerate particles.

* * * * *